(12) United States Patent
Sverdlik et al.

(10) Patent No.: US 9,028,417 B2
(45) Date of Patent: *May 12, 2015

(54) ULTRASOUND EMISSION ELEMENT

(75) Inventors: Ariel Sverdlik, Tel-Aviv (IL); Or Shabtay, Kibbutz Farod (IL)

(73) Assignee: CardioSonic Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/880,061

(22) PCT Filed: Oct. 18, 2011

(86) PCT No.: PCT/IB2011/054635
§ 371 (c)(1),
(2), (4) Date: Apr. 18, 2013

(87) PCT Pub. No.: WO2012/052921
PCT Pub. Date: Apr. 26, 2012

(65) Prior Publication Data
US 2013/0211292 A1  Aug. 15, 2013

Related U.S. Application Data

(63) Continuation-in-part of application No. 13/049,151, filed on Mar. 16, 2011, now Pat. No. 8,585,601.

(60) Provisional application No. 61/393,947, filed on Oct. 18, 2010.

(51) Int. Cl.
*A61B 8/14* (2006.01)
*A61N 7/02* (2006.01)
(Continued)

(52) U.S. Cl.
CPC *A61N 7/022* (2013.01); *A61N 1/05* (2013.01); *A61M 25/09* (2013.01);
(Continued)

(58) Field of Classification Search
CPC ............ A61N 7/022; A61N 2007/003; A61N 2007/0039; A61N 2007/0052; A61B 1/05; A61B 17/2202; A61B 6/12; A61B 6/485; A61B 2017/00106; A61B 2017/22008; A61B 2017/22051; A61B 2017/22081; A61B 8/12; A61B 8/0891; A61B 8/481; A61B 8/485; A61B 2018/0023; A61B 2018/00404; A61B 2018/00434; A61B 2018/00511; A61M 25/09
USPC .................................................. 600/437–469
See application file for complete search history.

(56) References Cited

U.S. PATENT DOCUMENTS

| 5,226,847 A | 7/1993 | Thomas, III et al. |
| 5,421,338 A | 6/1995 | Crowley et al. |

(Continued)

FOREIGN PATENT DOCUMENTS

| CN | 101610735 | 12/2009 |
| CN | 101820820 | 9/2010 |

(Continued)

OTHER PUBLICATIONS

Notice of Allowance Dated Jun. 21, 2013 From the US Patent and Trademark Office Re. U.S. Appl. No. 13/049,151.

(Continued)

*Primary Examiner* — Sanjay Cattungal

(57) ABSTRACT

There is provided in accordance with an exemplary embodiment of the invention an ultrasound catheter for intrabody medical therapy comprising; an element adapted to emit ultrasound energy; at least two electrodes configured to apply a voltage across at least some volume of the element; and a gas bubble containment area adapted to retain the gas bubble when in blood.

28 Claims, 23 Drawing Sheets

(51) Int. Cl.
  *A61N 1/05* (2006.01)
  *A61M 25/09* (2006.01)
  *A61M 25/06* (2006.01)
  *A61B 17/22* (2006.01)
  *A61B 8/00* (2006.01)
  *A61B 6/12* (2006.01)
  *A61B 6/00* (2006.01)
  *A61B 17/00* (2006.01)
  *A61B 19/00* (2006.01)
  *A61N 7/00* (2006.01)
  *A61B 8/12* (2006.01)
  *A61B 8/08* (2006.01)
  *A61B 18/00* (2006.01)

(52) U.S. Cl.
  CPC ....... *A61M 25/0662* (2013.01); *A61B 17/2202* (2013.01); *A61B 8/445* (2013.01); *A61B 6/12* (2013.01); *A61B 6/485* (2013.01); *A61B 2017/00106* (2013.01); *A61B 2017/22008* (2013.01); *A61B 2017/22051* (2013.01); *A61B 2017/22081* (2013.01); *A61B 2019/5276* (2013.01); *A61N 2007/003* (2013.01); *A61N 2007/0039* (2013.01); *A61N 2007/0052* (2013.01); *A61B 8/12* (2013.01); *A61B 8/0891* (2013.01); *A61B 8/481* (2013.01); *A61B 8/485* (2013.01); *A61B 2018/00023* (2013.01); *A61B 2018/00404* (2013.01); *A61B 2018/00434* (2013.01); *A61B 2018/00511* (2013.01); *A61N 2007/027* (2013.01)

(56) References Cited

U.S. PATENT DOCUMENTS

| | | |
|---|---|---|
| 5,467,251 A | 11/1995 | Katchmar |
| 5,524,630 A | 6/1996 | Crowley |
| 5,590,653 A | 1/1997 | Aida et al. |
| 5,620,417 A | 4/1997 | Jang et al. |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,895,355 A | 4/1999 | Schaer |
| 5,895,356 A | 4/1999 | Andrus et al. |
| 5,971,949 A | 10/1999 | Levin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,165,127 A | 12/2000 | Crowley |
| 6,210,393 B1 | 4/2001 | Brisken |
| 6,216,041 B1 | 4/2001 | Tierney et al. |
| 6,235,024 B1 | 5/2001 | Tu |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,511,428 B1 | 1/2003 | Azuma et al. |
| 6,527,759 B1 | 3/2003 | Tachibana et al. |
| 6,547,788 B1 | 4/2003 | Maguire et al. |
| 6,599,288 B2 | 7/2003 | Maguire et al. |
| 6,607,502 B1 | 8/2003 | Maguire et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De La Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 2001/0007940 A1 | 7/2001 | Tu et al. |
| 2001/0014780 A1 | 8/2001 | Martin et al. |
| 2002/0002371 A1 | 1/2002 | Acker et al. |
| 2002/0019627 A1 | 2/2002 | Maguire et al. |
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0125726 A1 | 7/2003 | Maguire et al. |
| 2003/0151417 A1 | 8/2003 | Koen |
| 2003/0181901 A1 | 9/2003 | Maguire et al. |
| 2003/0195496 A1 | 10/2003 | Maguire et al. |
| 2004/0006333 A1 | 1/2004 | Arnold et al. |
| 2004/0082859 A1 | 4/2004 | Schaer |
| 2004/0102769 A1 | 5/2004 | Schwartz et al. |
| 2005/0015079 A1 | 1/2005 | Keider |
| 2005/0020967 A1 | 1/2005 | Ono |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |

(56) References Cited

U.S. PATENT DOCUMENTS

| | | |
|---|---|---|
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0282407 A1* | 12/2007 | Demarais et al. ............. 607/113 |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0331686 A1 | 12/2010 | Hossack et al. |
| 2010/0331950 A1 | 12/2010 | Strommer |
| 2011/0034809 A1* | 2/2011 | Eberle et al. .................. 600/467 |
| 2011/0066217 A1 | 3/2011 | Diller et al. |
| 2011/0092781 A1 | 4/2011 | Gertner |
| 2011/0092880 A1 | 4/2011 | Gertner |
| 2011/0112400 A1 | 5/2011 | Emery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2012/0016273 A1 | 1/2012 | Diederich |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232436 A1 | 9/2012 | Warnking |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2013/0072928 A1 | 3/2013 | Schaer |
| 2013/0131668 A1 | 5/2013 | Schaer |
| 2013/0197555 A1 | 8/2013 | Schaer |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0267875 A1 | 10/2013 | Thapliyal et al. |
| 2014/0012133 A1 | 1/2014 | Sverdlik et al. |
| 2014/0039477 A1 | 2/2014 | Sverdlik et al. |
| 2014/0180197 A1 | 6/2014 | Sverdlik et al. |

FOREIGN PATENT DOCUMENTS

| | | |
|---|---|---|
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| WO | WO 91/10405 | 7/1991 |
| WO | WO 00/67648 | 10/2000 |
| WO | WO 01/45550 | 6/2001 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/061713 | 5/2012 |
| WO | WO 2013/030743 | 3/2013 |
| WO | WO 2013/111136 | 8/2013 |
| WO | WO 2013/157009 | 10/2013 |
| WO | WO 2013/157011 | 10/2013 |
| WO | WO 2014/188430 | 11/2014 |

OTHER PUBLICATIONS

Restriction Official Action Dated Jun. 28, 2013 From the US Patent and Trademark Office Re. U.S. Appl. No. 13/449,539.

International Search Report and the Written Opinion Dated Oct. 29, 2013 From the International Searching Authority Re. Application No. PCT/IL2013/050339.

Invitation to Pay Additional Fees Dated Jul. 24, 2013 From the International Searching Authority Re. Application No. PCT/IL2013/050068.

Official Action Dated Jul. 17, 2013 From the US Patent and Trademark Office Re. U.S. Appl. No. 13/049,013.

Official Action Dated May 8, 2013 From the US Patent and Trademark Office Re. U.S. Appl. No. 13/462,956.

Failla et al. "Sympathetic Tone Restrains Arterial Distensibility of Healthy and Atherosclerotic Subjects", Journal of Hypertension, 17: 1117-1123, 1999.

(56) References Cited

OTHER PUBLICATIONS

Grassi et al. "Sympathetic Mechanisms, Organ Damage, and Antihypertensive Treatment", Current Hypertension Report, 13: 303-308, 2011.

Kleinlogel et al. "A Gene-Fusion Strategy for Stoichiometric and Co-Localized Expression of Light-Gated Membrane Proteins", Nature Methods, 8(12): 1083-1091, Dec. 2011.

Lopez et al. "Effects of Sympathetic Nerves on Collateral Vessels in the Limb of Atherosclerosis Primates", Atherosclerosis, 90: 183-188, 1991.

Mangoni et al. "Effect of Sympathectomy on Mechanical Properties of Common Carotid and Femoral Arteries", Hypertension, 30: 1085-1088, 1997.

Olafsson et al. "Ultrasound Current Source Density Imaging", IEEE Transactions on Biomedical Engineering, 55(7): 1840-1848, Jul. 2008.

Swierblewska et al. "An Independent Relationship Between Muscle Sympathetic Nerve Activity and Pulse Wave Velocity in Normal Humans", Journal of Hypertension, 28: 979-984, 2010.

Wikswo Jr. et al. "Magnetic Field of a Nerve Impulse: First Measurements", Science, 208: 53-55, Apr. 4, 1980.

Witte et al. "Imaging Current Flow in Lobster Nerve Cord Using the Acoustoelectric Effect", Applied Physics Letters, 90: 163902-1-163902-3, 2007.

International Search Report and the Written Opinion Dated Sep. 19, 2013 From the International Searching Authority Re. Application No. PCT/IL2013/050068.

Official Action Dated Sep. 25, 2013 From the US Patent and Trademark Office Re. U.S. Appl. No. 13/462,956.

Lin et al. "Utility of the PlasmaKinetic™ Bipolar Forceps® for Control of the Renal Artery in a Porcine Model", JTUA, 14(3): 118-121, Sep. 2003.

Notice of Allowance Dated Nov. 7, 2013 From the US Patent and Trademark Office Re. U.S. Appl. No. 13/049,013.

Invitation to Pay Additional Fees Dated Aug. 5, 2013 From the International Searching Authority Re. Application No. PCT/IL2013/050341.

Schwartz "Strategies to Model Efficacy of Hypertension Devices", EuroPCR 2013, The Leading Cardiovascular Course, 24 P., 2013.

Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.

Official Action Dated Aug. 29, 2013 From the US Patent and Trademark Office Re. U.S. Appl. No. 13/449,539.

Invitation to Pay Additional Fees Dated Sep. 3, 2013 From the International Searching Authority Re. Application No. PCT/IL2013/050339.

International Preliminary Report on Patentability Dated May 2, 2013 From the International Bureau of WIPO Re. Application No. PCT/IB2011/054634.

International Preliminary Report on Patentability Dated May 2, 2013 From the International Bureau of WIPO Re. Application No. PCT/IB2011/054635.

International Preliminary Report on Patentability Dated May 2, 2013 From the International Bureau of WIPO Re. Application No. PCT/IB2011/054636.

International Preliminary Report on Patentability Dated May 2, 2013 From the International Bureau of WIPO Re. Application No. PCT/B2011/054638.

International Preliminary Report on Patentability Dated May 2, 2013 From the International Bureau of WIPO Re. Application No. PCT/IB2011/054639.

International Preliminary Report on Patentability Dated May 2, 2013 From the International Bureau of WIPO Re. Application No. PCT/IB2011/054640.

International Preliminary Report on Patentability Dated May 2, 2013 From the International Bureau of WIPO Re. Application No. PCT/IB2011/054641.

International Search Report and the Written Opinion Dated Feb. 7, 2012 From the International Searching Authority Re. Application No. PCT/IB2011/054641.

International Search Report and the Written Opinion Dated Jun. 22, 2012 From the International Searching Authority Re. Application No. PCT/IB2011/054640.

International Search Report and the Written Opinion Dated Jan. 23, 2012 From the International Searching Authority Re. Application No. PCT/IB2011/054635.

International Search Report and the Written Opinion Dated Jan. 25, 2012 From the International Searching Authority Re. Application No. PCT/IB2011/054636.

International Search Report and the Written Opinion Dated Jan. 27, 2012 From the International Searching Authority Re. Application No. PCT/IB2011/054634.

International Search Report and the Written Opinion Dated Jan. 27, 2012 From the International Searching Authority Re. Application No. PCT/IB2011/054638.

International Search Report and the Written Opinion Dated Jan. 31, 2012 From the International Searching Authority Re. Application No. PCT/IB2011/054639.

Invitation to Pay Additional Fees Dated Apr. 17, 2012 From the International Searching Authority Re. Application No. PCT/IB2011/054640.

Official Action Dated Oct. 24, 2012 From the US Patent and Trademark Office Re. U.S. Appl. No. 13/049,013.

Official Action Dated Jan. 29, 2013 From the US Patent and Trademark Office Re. U.S. Appl. No. 13/049,151.

Restriction Official Action Dated Oct. 5, 2012 From the US Patent and Trademark Office Re. U.S. Appl. No. 13/049,151.

Restriction Official Action Dated Aug. 30, 2012 From the US Patent and Trademark Office Re. U.S. Appl. No. 13/049,013.

Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.

Anonymus "Indication for and Results of Sympathectomy in Patients With Peripheral Vascular Disease", Lumbar Sympathectomy, Poster, 34 P., 2009.

Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.

Atherton et al. "Micro-Anatomy of the Renal Sympathetic Nervous System: A Human Postmortem Histologic Study", Clinical Anatomy, P.1-6, Oct. 4, 2011.

Bailey et al. "Cavitation Detection During Shock-Wave Lithotripsy", Ultrasound in Medicine and Biology, XP027605630, 31(9): 1245-1256, Sep. 1, 2005. Abstract, Fig. 1, P.1246, P.1247, r-h Col., P.1249, r-h Col.

Baker et al. "Operative Lumbar Sympathectomy for Severe Lower Limb Ischaemia: Still a Valuable Treatment Option", Annals of the Royal College of Surgeons of England, 76(1): 50-53, Jan. 1994.

Bharat et al. "Monitoring Stiffness Changes in Lesions After Radiofrequency Ablation at Different Temperatures and Durations of Ablation", Ultrasound in Medicine & Biology, 31(3): 415-422, 2005.

Blankestijn et al. "Renal Denervation: Potential Impact on Hypertension in Kidney Disease?", Nephrology, Dialysis, Transplantation, 26(9): 2732-2734, Apr. 19, 2011.

Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.

Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.

Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.

(56) References Cited

OTHER PUBLICATIONS

Brinton et al. "Externally Focused Ultrasound for Sympathetic Renal Denervation", WAVE I First-In-Man Study, Kona Medical Inc., PowerPont Presentation, TCT 2012, 15 P., 2012.

Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.

Campese et al. "Sympathetic Renal Innervation and Resistant Hypertension", International Journal of Hypertension, 2011(Art.ID 814354): 1-6, 2011.

Copty et al. "Localized Heating of Biological Media Using A 1-W Microwave Near-Field Probe", IEEE Transactions on Microwave Theory and Techniques, 52(8): 1957-1963, Aug. 2004.

Copty et al. "Low-Power Near-Field Microwave Applicator for Localized Heating of Soft Matter", Applied Physics Letters, 84(25): 5109-5111, Jun. 21, 2004.

Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.

Davies et al. "First-in-Man Safety Evaluation of Renal Denervation for Chronic Systolic heart Failure: Primary Outcome From REACH-Pilot Study", International Journal of Cardiology, 162: 189-192, 2013.

Deneke et al. "Histopathology of Intraoperatively Induced Linear Radiofrequency Ablation Lesions in Patients With Chronic Atrial Fibrillation", European Heart Journal, 26: 1797-1803, 2005.

DiBona "Neural Control of Renal Function: Cardiovascular Implications", Hypertension, 13: 539-548, 1989.

DiBona "Neural Control of the Kidney: Past, Present, and Future", Hypertension, 41: 621-624, Dec. 16, 2002.

DiBona "Physiology in Perspective: The Wisdom of the Body. Neural Control of the Kidney", American Journal of Physiology, Regulatory, Integrative and Comparative Physiology, 289(3): R633-R641, Sep. 2005.

DiBona et al. "Differentiated Sympathetic Neural Control of the Kidney", American Journal of Physiology, 271: R84-R90, 1996.

DiBona et al. "Translational Medicine: The Antihypertensive Effect of Renal Denervation", American Journal of Physiology, Regulatory, Integrative and Comparative Physiology, 298(2): R245-R253, Feb. 2010.

Diederich et al. "Induction of Hyperthermia Using an Intracavitary Multielement Ultrasonic Applicator", IEEE Transactions on Biomedical Engineering, 36(4): 432-438, Apr. 1989.

Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.

Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.

Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.

Fort Wayne Metals "HHS Tube", Fort Wayne Metals Research Products Corporation, 2 P., 2009.

Fujikura et al. "Effects of Ultrasonic Exposure Parameters on Myocardial Lesions Induced by High-Intensity Focused Ultrasound", Journal of Ultrasound Medicine, 25: 1175-1186, 2006.

Glazier et al. "Laser Balloon Angioplasty Combined With Local Intrcoronary Heparin Therapy: Immediate and Short-Term Follow-Up Results", American Heart Journal, 134: 266-273, 1997.

Goswami "Renal Denervation: A Percutaneous Therapy for HTN", Prairie Heart Institute, Synvacor, The VEINS: Venous Endovascular Interventions Strategies, Chicago, USA, 42 P., 2012.

Granada et al. "A Translational Overview for the Evaluation of Pen-Renal Denervation Technologies", Cardiovascular Research Foundation, Columbai University Medical Center, New York, USA, Alizee Pathology, 25 P., 2011.

Griffiths et al. "Thoraco-Lumbar Splanchnicectomy and Sympathectomy. Anaesthetic Procedure", Anaesthesia, 3(4): 134-146, Oct. 1948.

Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.

Hering et al. "Renal Denervation in Moderate to Severe CKD", Journal of the American Society of Nephrology, 23: 1250-1257, 2012.

Hering et al. "Substantial Reduction in Single Sympathetic Nerve Firing After Renal Denervation in Patients With rRsistant Hypertension", Hypertension, 61: 1-14, Nov. 19, 2012.

Janssen et al. "Role of Afferent Renal Nerves in Spontaneous Hypertension in Rats", Hypertension, 13: 327-333, 1989.

Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.

Katholi "Renal Nerves in the Pathogenesis of Hypertension in Experimental Animals and Humans", American Journal of Physiology, 245: F1-F14, 1983.

Katholi et al. "Intrarenal Adenosine Produces Hypertension by Activating the Sympathetic Nervous System Via the Renal Nerves in the Dog", Journal of Hypertension, 2: 349-359, 1984.

Katholi et al. "Renal Nerves in the Maintenance of Hypertension: A Potential Therapeutic Target", Current Hypertension Reports, 12(3): 196-204, Jun. 2010.

Kline et al. "Functional Reinnervation and Development of Supersensitivity to NE After Renal Denervation in Rats", American Journal of Physiology, 238: R353-R358, 1980.

Kolh "Carotid Denervation by Adventitial Stripping: A Promising Treatment of Carotid Sinus Syndrome?", European Journal of Vascular and Endovascular Surgery, 39(2): 153-154, Feb. 2010.

Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.

Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.

Lambert et al. "Redo of Percutaneous Renal Denervation in a Patient With Recurrent Resistant Hypertension After Primary Treatment Success", Catheterization and Cardiovascular Interventions, P.1-11, 2012.

Lele "Effects of Focused Ultrasonic Radiation on Peripheral Nerve, With Observations on Local Heating", Experimental Neurology, 8: 47-83, 1963.

Lemoine et al. "Amputations and Sympathectomy in Peripheral Vascular Disease of the Lower Extremity. Experience With 180 Patients", Journal of the National Medical Association, 61(3): 219-221, May 1969.

Li et al. "Acoustic Proximity Ranging in the Presence of Secondary Echoes", IEEE Transactions on Instrumentation and Measurement, XP011102759, 52(5): 1593-1605, Oct. 1, 2003. P.1593.

Liu et al. "A Helical Microwave Antenna for Welding Plaque During Balloon Angioplasty", IEEE Transactions on Microwave Theory and Techniques, 44(10): 1819-1831, Oct. 1996.

Mabin et al. "First Experience With Endovascular Ultrasound Renal Denervation for the Treatment of Resistant Hypertension", EuroIntervention, 8: 57-61, 2012.

Mahfoud et al. "Effect of Renal Sympathetic Denervation on Glucose Metabolism in Patients With Resistant Hypertension: A Pilot Study", Circulation, 123: 1940-1946, 2011.

Mahfoud et al. "Is There a Role for Renal Sympathetic Denervation in the Future Treatment of Resistant Hypertension?", Future Cardiology, 7(5): 591-594, 2011.

Mahfoud et al. "Renal Hemodynamics and Renal Function After Catheter-Based Renal Sympathetic Denervation in Patients With Resistant Hypertension", Hypertension, 60: 419-424, 2012.

(56) References Cited

OTHER PUBLICATIONS

Makris et al. "Resistant Hypertension Workup and Approach to Treatment", International Journal of Hypertension, 2011(Art. ID598694): 1-10, 2011.

Manasse et al. "Clinical Histopathology and Ultrstructural Analysis of Myocardium Following Microwave Energy Ablation", European Journal of Cardio-Thoracic Surgery, 23: 573-577, 2003.

Martin et al. "Premise, Promise, and Potential Limitations of Invasive Devices to Treat Hypertension", Current Cardiology Reports, 13(1): 86-92, Feb. 2011.

Mazor "Efficacy of Renal Denervation Is Positively Impacted by Longitudinal Treatments", Vessix Vascular Inc., PowerPoint Presentation, TCT 2012, 20 P., 2012.

Mogil et al. "Renal Innervation and Renin Activity in Salt Metabolism and Hypertension", American Journal of Physiology, 216(4): 693-697, Apr. 1969.

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.

Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

Ong et al. "Successful Treatment of Resistant Hypertension With Percutaneous Renal Denervation Therapy", Heart, 98(23): 1754-1755, Dec. 2012.

Ormiston "One Shot (Covidien)", Maya Medical, Auckland, New Zealand, PowerPoint Presentation.

Ormiston et al. "First-in-Human Use of the OneShot™ Renal Denervation System From Covidien", EuroIntervention, 8: 1090-1094, 2013.

Page et al. "The Effect of Renal Denervation on Patients Suffering From Nephritis", The Journal of Clinical Investigation, 14(4): 443-458, Jul. 1935.

Papademetriou et al. "Renal Sympathetic Denervation for the Treatment of Difficult-to-Control or Resistant Hypertension", International Journal of Hypertension, 2011 (Art.ID196518): 1-8, Jan. 2011.

Para Tech Coating "Parylene Properties", Para Tech Coating Inc 1 P.

Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.

Prochnau et al. "Catheter-Based Renal Denervation for Drug-Resistant Hypertension by Using a Standard Electrophysiology Catheter", EuroIntervention, 7: 1077-1080, 2012.

Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.

Quinn "Pre-Eclampsia and Partial Uterine Denervation", Medical Hypotheses, 64(3): 449-454, 2005. Abstract.

Rappaport "Treating Cardiac Disease With Catheter-Based Tissue Heating", IEEE Microwave Magazine, p. 57-64, Mar. 2002.

Rothman "FIM Evaluation of a New, Multi-Electrode RF System for Renal Denervation (Medtronic)", Medtronic Inc., PowerPoint Presentation, 8 P., 2012.

Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.

Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.

Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.

Sanni et al. "Is Sympathectomy of Benefit in Critical Leg Ischaemia Not Amenable to Revascularisation?", Interactive CardioVascular and Thoracic Surgery, 4: 478-483, 2005.

Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.

Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.

Schlaich et al. "Renal Sympathetic-Nerve Ablation for Uncontrolled Hypertension", New England Journal of Medicine, 361(9): 932-934, Aug. 27, 2009.

Sievert et al. "Catheter-Based Technology Alternatives for Renal Denervation", CardioVascular Center Frankfurt, Germany, TCT 2012, Miami, FL, USA Oct. 22-26, 2012, PowerPoint Presentation, 35 P., Oct. 2012.

Souchon et al. "Monitoring the Formation of Thermal Lesions With Heat-Induced Echo-Strain Imaging: A Feasibility Study", Ultrasound in Medicine & Biology, 31(2): 251-259, 2005.

Stefanadis "Vincristine Local Delivery for Renal Artery Denervation", Athens, Greece, PowerPoint Presentation, TCT 2012, 21 P., 2012.

Steigerwald et al. "Morphological Assessment of Renal Arteries After Radiofrequency Catheter-Based Sympathetic Denervation in A Porcine Model", Journal of Hypertension, 30(11): 2230-2239, Nov. 2012.

Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.

Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.

Szabo "Diagnostic Ultrasound Imaging: Inside Out", Academic Press Series in Biomedical Engineering, 2004. Book: Diagnostic Ultrasound Imaging Inside Out—Bronzino ; Academic Press Series in Biomedical Engineering- ,Joseph Bronzino, Series Editor ; Trinity College—Hartford, Connecticut "Diagnostic Ultrasound Imaging Inside Out", Academic Press Series in Biomedical Engineering, 2004.

Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.

Toorop et al. "Clinical Results of Carotid Denervation by Adventitial Stripping in Caotid Sinus Syndrome", Europan Journal of Vascular and Endovascular Syndrome, 39: 146-152, 2010.

Tyreus et al. "Two-Dimensional Acoustic Attenuation Mapping of High-Temperature Interstitial Ultrasound Lesions", Physics in Medicine and Biology, 49: 533-546, 2004.

Virmani "Translation Medicine and Renal Denervation: Pre-Clinical Animal Models and Histoanatomy", CVPath Institute, Gaithersburg, MD, USA PowerPoint Presentation.

Voskuil et al. "Percutaneous Renal Denervation for the Treatment of Resistant Essential Hypertension; The First Dutch Experience", Netherlands Heart Journal, 19(7-8): 319-323, Aug. 2011.

Warwick et al. "Trackless Lesions in Nervous Tissues Produced by High Intensity Focused Ultrsound (High-Frequency Mechanical Waves)", Journal of Anatomy, 102(3): 387-405, 1968.

Wilcox "Resistant Hypertension and the Role of the Sympathetic Nervous System", Medtronic, 30 P.

Williams et al. "Laser Energy Source in Surgical Atrial Fibrillation Ablation: Preclinical Experience", The Annals of Thoracic Surgery, 82: 2260-2264, 2006.

(56) References Cited

OTHER PUBLICATIONS

Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Xu et al. "Experimental Nerve Thermal Injury", Brain, 117: 375-384, 1994.
International Search Report and the Written Opinion Dated Oct. 11, 2013 From the International Searching Authority Re. Application No. PCT/IL2013/050341.
Official Action Dated Dec. 19, 2013 From the US Patent and Trademark Office Re. U.S. Appl. No. 13/049,022.
Communication Pursuant to Article 94(3) EPC Dated Nov. 4, 2014 From the European Patent Office Re. Application No. 11833950.6.
Communication Pursuant to Article 94(3) EPC Dated Oct. 30, 2014 From the European Patent Office Re. Application No. 11782221.3.
International Preliminary Report on Patentability Dated Oct. 30, 2014 From the International Bureau of WIPO Re. Application No. PCT/IL2013/050341.
International Search Report and the Written Opinion Dated Nov. 20, 2014 From the International Searching Authority Re. Application No. PCT/IL2014/050457.
Official Action Dated Nov. 4, 2014 From the US Patent and Trademark Office Re. U.S. Appl. No. 13/879,400.
Official Action Dated Nov. 5, 2014 From the US Patent and Trademark Office Re. U.S. Appl. No. 13/049,022.
Restriction Official Action Dated Nov. 17, 2014 From the US Patent and Trademark Office Re. U.S. Appl. No. 13/880,066.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Drake et al. "Problematic Anatomical Sites Around the Pulmonary Artery", Gray's Anatomy for Students, 9 P., 2004.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.
Schelegle et al. "Vagal Afferents Contribute to Exacerbates Airway Responses Following Ozone and Allergen Challenge", Respiratory Physiology & Neurobiology, 181(3): 277-285, May 31, 2012.
Applicant-Initiated Interview Summary Dated Jan. 24, 2014 From the US Patent and Trademark Office Re. U.S. Appl. No. 13/449,539.
Communication Pursuant to Article 94(3) EPC Dated Jun. 10, 2014 From the European Patent Office Re. Application No. 117822476.3.
Communication Pursuant to Article 94(3) EPC Dated Jun. 10, 2014 From the European Patent Office Re. Application No. 11784782.2.
Communication Pursuant to Article 94(3) EPC Dated Apr. 14, 2014 From the European Patent Office Re. Application No. 11782221.3.
Communication Pursuant to Article 94(3) EPC Dated Sep. 26, 2014 From the European Patent Office Re. Application No. 11782222.1.
Communication Under Rule 71(3) EPC Dated 24 Apr. 24 2014 From the European Patent Office Re. Application No. 11782223.9.
International Preliminary Report on Patentability Dated Aug. 7, 2014 From the International Bureau of WIPO Re. Application No. PCT/IL2013/050068.
International Preliminary Report on Patentability Dated Oct. 30, 2014 From the International Bureau of WIPO Re. Application No. PCT/IL2013/050339.
Invitation Pursuant to Rule 137(4) EPC Dated Apr. 4, 2014 From the European Patent Office Re. Application No. 11785792.0.
Invitation Pursuant to Rule 137(4) EPC Dated Apr. 8, 2014 From the European Patent Office Re. Application No. 11782222.1.
Invitation Pursuant to Rule 137(4) EPC Dated Apr. 10, 2014 From the European Patent Office Re. Application No. 11782476.3.
Invitation to Pay Additional Fees Dated Sep. 4, 2014 From the International Searching Authority Re. Application No. PCT/IL2014/050457.
Office Action Dated Jul. 30, 2014 From the State Intellectual Property Office of the People's Republic of China Re. Application No. 201180060741.3 and Its Summary in English.
Official Action Dated Oct. 7, 2014 From the US Patent and Trademark Office Re. U.S. Appl. No. 13/880,109.
Official Action Dated Sep. 10, 2014 From the US Patent and Trademark Office Re. U.S. Appl. No. 14/049,238.
Official Action Dated Apr. 14, 2014 From the US Patent and Trademark Office Re. U.S. Appl. No. 13/879,400.
Official Action Dated Mar. 20, 2014 From the US Patent and Trademark Office Re. U.S. Appl. No. 13/449,539.
Restriction Official Action Dated Jul. 7, 2014 From the US Patent and Trademark Office Re. U.S. Appl. No. 14/049,238.
Restriction Official Action Dated Oct. 30, 2014 From the US Patent and Trademark Office Re. U.S. Appl. No. 13/880,083.
Search Report Dated Jul. 17, 2014 From The State Intellectual Property Office of the People's Republic of China Re. Application No. 201180060741.3 and Its Machine Translation in English.
Supplementary European Search Report Dated Mar. 12, 2014 From the European Patent Office Re. Application No. 11833950.6.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Gander et al. "Least-Squares Fitting of Circles and Ellipses", BIT Numerical Mathematics, 34(4): 558-578, Dec. 1994.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Lafon "Miniature Devices for Minimally Invasive Thermal Ablation by High Intensity Ultrasound", Cargese Workshop 2009, University of Lyon, France, INSERM U556, Presentation, 39 P., 2009.

(56) References Cited

OTHER PUBLICATIONS

Reddy "Sound Intervention", Mount Sinai School of Medicine, MSSM, Presentation, 19 P., 2012.

Tibshirani "Regression Shrinkage and Selction Via the Lasso: A Retrospective", Journal of the Royal Statistical Society, Series B: Statistical Methodology, 73(Pt.3): 273-282, 2011.

Tibshirani "Regression Shrinkage and Selection Via the Lasso", Journal of the Royal Statistical Society, Series B: Methodological, 58(1): 267-288, 1996.

Zeller "Percutaneous Renal Denervation System. The New Ultrasound Solution for the Mangament of Hypertension", Paradise Ultrasound Denervation System, ReCor Medical, 27 P., 2013.

Applicant-Initiated Interview Summary Dated Jan. 21, 2015 From the US Patent and Trademark Office Re. U.S. Appl. No. 13/449,539.

Notification of Office Action and Search Report Dated Dec. 1, 2014 From The State Intellectual Property Office of the People's Republic of China Re. Application No. 201180060862.8.

Official Action Dated Dec. 3, 2014 From the US Patent and Trademark Office Re. U.S. Appl. No. 13/462,956.

* cited by examiner

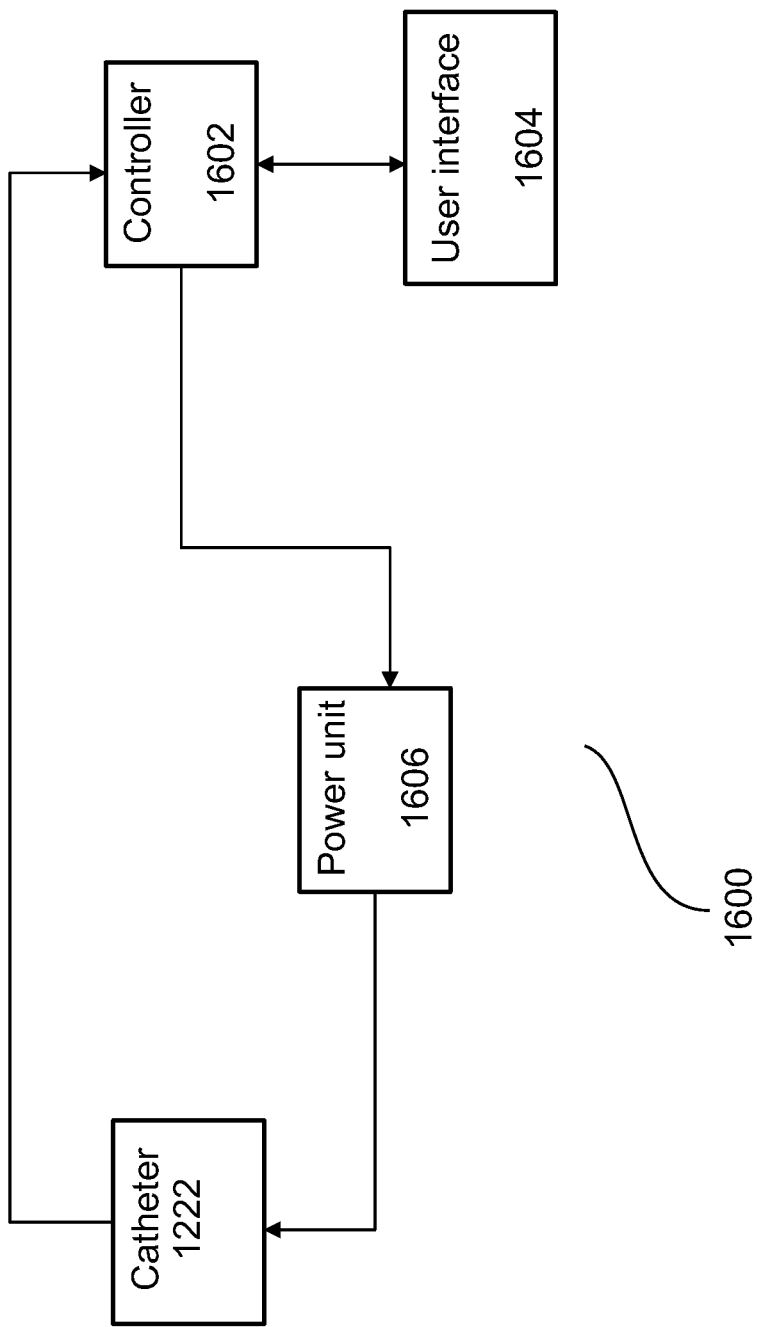

ULTRASOUND EMISSION ELEMENT

RELATED APPLICATIONS

This application is a National Phase of PCT Patent Application No. PCT/IB2011/054635 having International filing date of Oct. 18, 2011, which is a continuation-in-part (CIP) of pending U.S. patent application Ser. No. 13/049,151 filed on Mar. 16, 2011, and which claims the benefit of priority under 35 USC §119(e) of U.S. Provisional Patent Application No. 61/393,947 filed on Oct. 18, 2010.

U.S. patent application Ser. No. 13/049,151 claims the benefit of priority under 35 USC §119(e) of U.S. Provisional Patent Application No. 61/393,947 filed on Oct. 18, 2010.

The contents of the above applications are all incorporated by reference as if fully set forth herein in their entirety.

The present application is related to co-filed, co-pending and co-assigned patent applications entitled:

"THERAPEUTICS RESERVOIR" (PCT Patent Application No. PCT/IB2011/054634 filed Oct. 18, 2011), which teaches an apparatus and a method for forming a drug reservoir as a possible application of the ultrasound energy application described herein;

"AN ULTRASOUND TRANSCEIVER AND CONTROL OF A THERMAL DAMAGE PROCESS" (PCT Patent Application No. PCT/IB2011/054639 filed on Oct. 18, 2011), which teaches an apparatus and method for performing ultrasonic imaging, such as to provide feedback about the effect of treatment on tissues as described herein;

"AN ULTRASOUND TRANSCEIVER AND USES THEREOF" (PCT Patent Application No. PCT/IB2011/054636 filed on Oct. 18, 2011), which teaches a method for feedback and control of the ultrasonic emission element, such as to use the same ultrasonic element for treatment and imaging, potentially useful when treating and imaging as described herein;

"AN ULTRASOUND TRANSCEIVER AND COOLING THEREOF" (PCT Patent Application No. PCT/IB2011/054641 filed on Oct. 18, 2011), which teaches a method for cooling of the ultrasonic emission element, potentially useful when applying energy as described herein;

"SEPARATION DEVICE FOR ULTRASOUND ELEMENT" (PCT Patent Application No. PCT/IB2011/054638 filed on Oct. 18, 2011), which teaches a device to prevent the ultrasonic emission element from touching the blood vessel wall, potentially useful for preventing damage to the intima layer when applying energy as described herein; and "TISSUE TREATMENT" (PCT Patent Application No. PCT/IB2011/054640 filed on Oct. 18, 2011), which teaches a method of selectively targeting and treating tissues using ultrasound, potentially useful when applying energy as described herein;

the disclosures of which are incorporated herein by reference.

FIELD AND BACKGROUND OF THE INVENTION

The present invention, in some embodiments thereof, relates to an ultrasound emission element and, more particularly, but not exclusively, to a system for delivering ultrasound energy for medical treatment, for example, intravascular treatment, for example, using an ultrasound catheter.

Maguire and Peacock, in EP 1769759 disclose:

"A medical device assembly and method provides an ultrasound transducer (904) mounted onto a delivery member, such as the elongate body (802) of a catheter shaft, without a support structure bridging between a separation area between the transducer and the shaft. Mounting flanges extend from either end of the transducer and are mounted at first and second locations along the catheter shaft such that the transducer is not in mechanical contact with the catheter shaft between those mounting locations to provide for air backing between the transducer and the catheter shaft so as to isolate ultrasound transmission radially away from the catheter shaft and toward the tissue surrounding the shaft. The transducer is substantially "airbacked" when mounted onto a delivery member in accordance with the present invention."

Sverdlik et al, in PCT/IL2008/000234, filed FEB 21, 2008 disclose:

"Described is a method of stabilizing blood vessel wall abnormality. The method includes ultrasonically heating at least a portion of the blood vessel wall having the abnormality; monitoring a parameter related to a property of at least a portion of the heated portion of the blood vessel wall; and stopping the heating when the monitored parameter changes by a predetermined factor or after the monitored parameter changes in a slow enough rate."

Additional background art includes:
U.S. Pat. No. 5,699,804
U.S. Pat. No. 7,410,486
U.S. Pat. No. 7,621,929
U.S. Pat. No. 7,717,948
U.S. Pat. No. 7,771,372
US patent application 2008228111
US patent application 2009216246
US patent application 2010091112

SUMMARY OF THE INVENTION

An aspect of some embodiments of the invention relates to an ultrasound emission element for medical therapy comprising an element adapted to transmit ultrasound energy. Optionally, the element is coupled to a gas bubble. Alternatively or additionally, the element is suspended, providing for a relatively low damping force during function.

There is provided in accordance with an exemplary embodiment of the invention an ultrasound catheter for intrabody medical therapy comprising; an element adapted to transmit ultrasound energy; at least two electrodes configured to apply a voltage across at least some volume of the element; and a gas bubble containment area adapted to retain the gas bubble when in blood.

In an exemplary embodiment of the invention, the catheter further comprises, a support board that is coupled to the element, wherein the gas bubble is retained in a space between the board and the element. Optionally, at least some surface area of at least the element and the board comprise a coating adapted to retain the bubble to the element. Optionally, the coating comprises parylene. Optionally, the board comprises a depression or an aperture, and the element is positioned over at least some volume of the depression or the aperture.

In an exemplary embodiment of the invention, the element is rectangular.

In an exemplary embodiment of the invention, the element comprises irregularities on a surface to couple the bubble to the element by increasing an area of the surface.

In an exemplary embodiment of the invention, the gas comprises selecting from the group consisting of: air, oxygen, nitrogen, carbon dioxide, carbon tetrafluoride.

In an exemplary embodiment of the invention, at least two bubbles coupled to a side of the element.

In an exemplary embodiment of the invention, the catheter comprises a housing, the housing coupled to the board. Optionally, the housing comprises a heat sink thermally coupled to the element.

In an exemplary embodiment of the invention, the catheter further comprises a canopy surrounding the element; and fluid between the element and the canopy. Optionally, the fluid comprises a circulating fluid.

There is provided in accordance with an exemplary embodiment of the invention an ultrasound catheter for medical therapy comprising a support board, an element adapted to transmit ultrasound energy, the element suspended by the board; and at least two electrodes configured to apply a voltage across at least some volume of the element.

In an exemplary embodiment of the invention, the element is configured to produce a relatively non-diverging ultrasound beam.

In an exemplary embodiment of the invention, the element is suspended a distance above the board. Optionally, the element is suspended by a material raised above a surface of the board. Optionally, the material includes copper. Optionally, the material includes an electrically conductive glue.

In an exemplary embodiment of the invention, the element is suspended over an aperture or a depression in the board by walls of the aperture or depression. Optionally, the element is suspended over the board along the periphery of the element. Optionally, the element is suspended over the board away from the periphery of the element.

In an exemplary embodiment of the invention, the board further comprises at least one heat conductive element thermally coupled to the element. Optionally, a cross section of the support board is annular.

In an exemplary embodiment of the invention, two or more elements adapted to transmit ultrasound energy, at least one of the two or more elements is supported above the board, and at least one gas bubble coupled to at least one of the two or more elements.

In an exemplary embodiment of the invention, the catheter further comprises: an element comprising at least one region adapted to at least transmit and at least one region adapted to at least receive, the element positioned over the board; at least two electrodes configured to apply a voltage across at least some volume of the regions; and at least one gas bubble coupled to the at least one region adapted to at least transmit.

In an exemplary embodiment of the invention, the catheter further comprises: two or more elements adapted to transmit ultrasound energy, at least two of the two or more elements are supported by the board; at least two electrodes configured to apply a voltage across at least some volume of the two or more elements; and a gas bubble coupled to at least two elements of the at least two elements. Optionally, the two or more elements are used as a phased array.

There is provided in accordance with an exemplary embodiment of the invention an ultrasound catheter for medical therapy comprising: an element adapted to transmit ultrasound energy; at least two electrodes configured to apply a voltage across at least some volume of the element; and a support board, the element suspended by the board and the board comprises at least one channel to direct flow of a fluid between the board and the element.

In an exemplary embodiment of the invention, the element comprises at least one region adapted to at least transmit ultrasound treatment.

In an exemplary embodiment of the invention, the element comprises at least one region adapted to at least receive ultrasound imaging.

In an exemplary embodiment of the invention, the board comprises a depression comprising a damping material, and wherein the one region adapted to at least receive is coupled to the damping material.

There is provided in accordance with an exemplary embodiment of the invention a method of making an ultrasound catheter for medical therapy comprising: applying a gas to an element adapted to transmit ultrasound energy; forming a bubble comprising a gas surrounded by a film of a liquid; and retaining the bubble by immersing the element in a liquid.

There is provided in accordance with an exemplary embodiment of the invention a catheter for medical therapy comprising: a distal end; and a proximal end comprising: an ultrasound catheter comprising an acoustic element; and a temperature sensor for estimating the temperature of the element. Optionally, the sensor is positioned downstream from the element.

There is provided in accordance with an exemplary embodiment of the invention a catheter for medical therapy comprising: a distal end; and a proximal end comprising: an ultrasound catheter comprising an acoustic element; and at least one cooling element thermally coupling the element to a heat sink.

In an exemplary embodiment of the invention, the heat sink comprises one or more braids in a shaft of the catheter.

In an exemplary embodiment of the invention, the cooling element comprises one or more channels on the surface of the catheter, the grooves configured to direct flow of a fluid over the element.

In an exemplary embodiment of the invention, the cooling element controls the flow rate of a fluid over the element.

In an exemplary embodiment of the invention, the distal end is made out of relatively stiff materials and a proximal end is made out of relatively flexible materials.

In an exemplary embodiment of the invention, a shaft of the catheter is configured to transmit torque in a one to one ratio from the distal end to the proximal end.

There is provided in accordance with an exemplary embodiment of the invention an ultrasound catheter for medical therapy comprising: an element adapted to transmit ultrasound energy; at least two electrodes configured to apply a voltage across at least some volume of the element; and a support board, wherein the support board is coupled to the element at 0.06%-17% of a surface area of the board.

In an exemplary embodiment of the invention, the catheter further comprises electrically conductive glue to couple the element to the board.

There is provided in accordance with an exemplary embodiment of the invention an ultrasound system for medical therapy comprising: an ultrasound catheter; a catheter comprising the catheter at a distal end; and a controller, the controller configured to apply electrical power to the catheter to output ultrasound energy at a frequency of 10-60 Mhz and at an intensity of over 10 Watts per square centimeter.

There is provided in accordance with an exemplary embodiment of the invention a catheter for medical therapy comprising: a distal end; and a proximal end comprising: an ultrasound catheter comprising an acoustic element; wherein the catheter is designed to not contact a vessel wall while the catheter is aimed at the vessel wall.

In an exemplary embodiment of the invention, an ultrasound beam produced by the catheter is non-focused.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 16 is a block diagram of a control system, in accordance with an exemplary embodiment of the invention.

DESCRIPTION OF SPECIFIC EMBODIMENTS OF THE INVENTION

Figure 1:
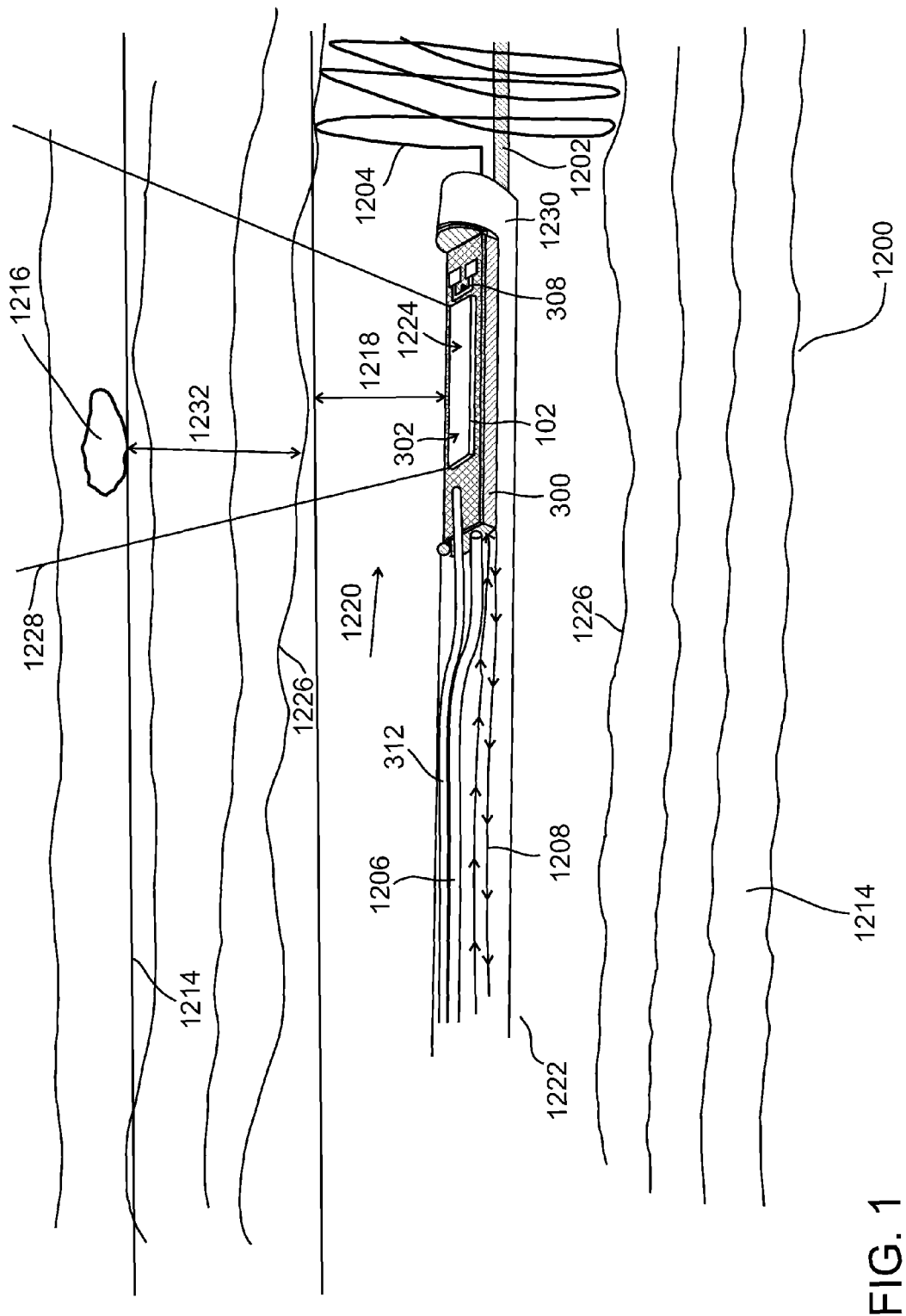
FIG. 1 is an illustration of a catheter, in accordance with an exemplary embodiment of the invention.

The present invention, in some embodiments thereof, relates to an ultrasound emission element and, more particularly, but not exclusively, to a system for delivering ultrasound energy for medical treatment, for example, intravascular treatment.

An aspect of some embodiments of the invention relates to an ultrasound transducer comprising an acoustic element (e.g., ultrasound emission element) coupled to a gas bubble. Optionally, two or more bubbles are coupled to the element. Optionally, the bubble is created when the transducer is inserted into a fluid.

In an exemplary embodiment of the invention, two or more electrodes are positioned to create a voltage across at least some volume of the element.

An aspect of some embodiments of the invention relates to the gas bubble remaining coupled to the element during vibrations, for example 5-60 Mhz, 10-20 Mhz, or other smaller, intermediate or larger frequency ranges, that produce an ultrasound intensity sufficient for medical therapy, for example 20 watts/$cm^2$, 30 watts/$cm^2$, 50 watts/$cm^2$, 100 watts/$cm^2$, or other smaller, intermediate or larger intensities.

In an exemplary embodiment of the invention, the relatively high acoustic intensity output is achieved by the use of the bubble.

In an exemplary embodiment of the invention, the bubble is coupled to the element by surface tension. Alternatively or additionally, the coupling surface area of the element is increased, for example, by one or more of, hair-like projections, tree-like projections, small spheres, jagged irregularities. Alternatively or additionally, the coupling force is increased by a coating at least on the element, for example, a hydrophilic coating and/or a hydrophobic coating. Alternatively or additionally, static electricity forms and/or increases the coupling.

An aspect of some embodiments of the invention relates to making an ultrasound transducer comprising a bubble coupled to an acoustic element. In an exemplary embodiment of the invention, the method of making comprises forming the bubble by submersion of the element in a liquid such as water, saline, blood. Alternatively or additionally, the method comprises forming the bubble from a liquid and/or coupling the bubble to the element.

In an exemplary embodiment of the invention, the bubble is filled with a gas, for example, one or more of, room air, oxygen, nitrogen, carbon dioxide, carbon tetraflouride.

An aspect of some embodiments of the invention relates to an acoustic element suspended over and/or above a support board, at a relatively small number of locations, for example, 1, 2, 8, 12 or other smaller, intermediate or larger numbers, and/or at a relatively small surface area of the element, for example, about 0.06%-about 17% of the surface area of the element, for example, one location is about 0.06% of the surface area, eight locations are about 0.5% of the surface area. Optionally, the acoustic element is coupled to a bubble. Optionally, the suspension areas are at a peripheral location of the element. Alternatively or additionally, the suspension areas are away from the periphery. In an exemplary embodiment of the invention, suspension relatively decreases the damping forces on the element.

In an exemplary embodiment of the invention, surface features on the board control and/or direct flow of a liquid between the board and the element. Optionally, the surface features are grooves.

In an exemplary embodiment of the invention, at least some area of the element is suspended over and/or above a depression and/or an aperture in the board and/or in a housing. Optionally, at least some of the depression and/or aperture is configured for a function, for example, one or more of, reflection, transmission, damping.

In an exemplary embodiment of the invention, the transducer comprising at least two elements suspended over and/or above a board. Optionally, at least one element is coupled to at least one bubble. Alternatively or additionally, at least one bubble is coupled to at least two elements.

An aspect of some embodiments of the invention relates to a transducer comprising at least two regions configured for at least two different functions. Optionally, at least one region is configured for imaging (e.g., transmitting and/or receiving) and/or at least one region is configured for treatment. Optionally, two or more regions (e.g., at two or more different location) configured for treatment are designed to operate at two or more different frequencies.

An aspect of some embodiments of the invention relates to at least one cooling element reducing the temperature of the element. Optionally, cooling occurs according to the temperature measured by the sensor. Optionally, cooling occurs by a flow of a liquid (e.g., blood, saline, dye) over the element, for example, by injection of the liquid, by passive flow of the liquid (e.g., blood flow), by acoustic pressure induced flow, by active control of the flow rate of the liquid, by directing flow of the liquid using one or more flow channels (e.g., on the catheter). Alternatively or additionally, cooling occurs by transfer of heat to blood, for example, through the surface of the catheter shaft and/or the transducer surface. Optionally, cooling is increased using active heat flux such as a thermoelectric cooler.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview

Figure 2:
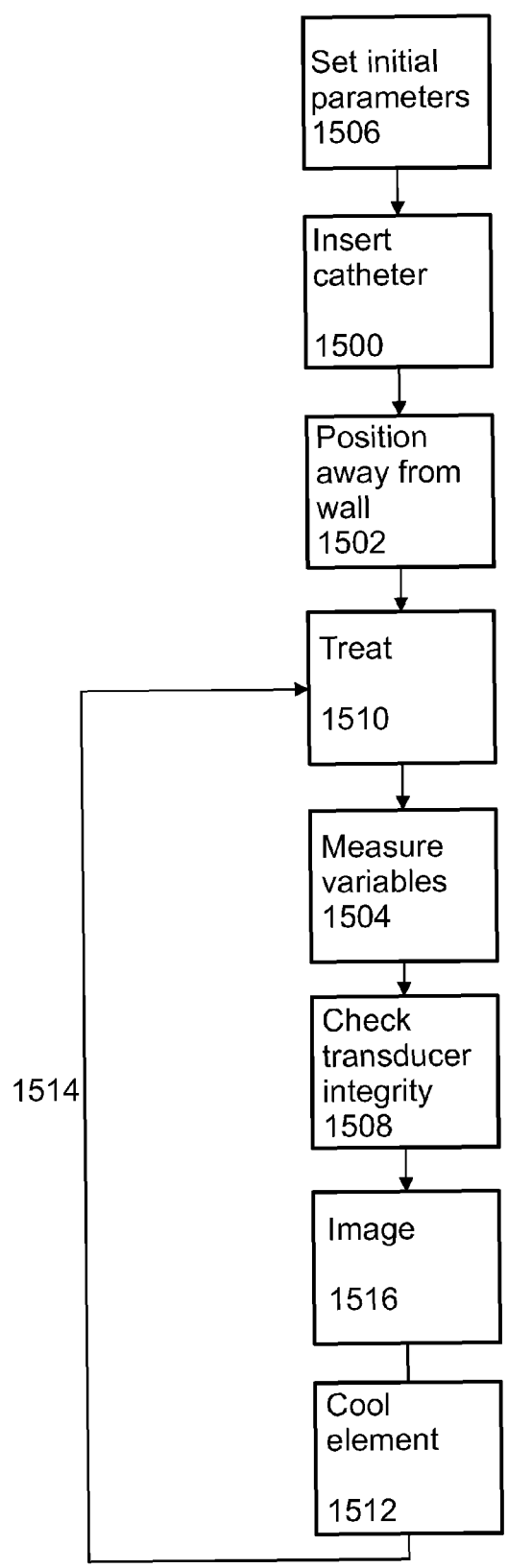
FIG. 2 is a flow chart of a treatment method, in accordance with an exemplary embodiment of the invention.

For purposes of better understanding some embodiments of the invention, as illustrated in FIGS. 3-16 of the drawings, reference is first made to an example of an ultrasound treatment catheter 1222 inside a blood vessel, as illustrated in FIG. 1, and/or a method of treatment, as illustrated in FIG. 2, where exemplary embodiments of the invention may be used.

At 1506, one or more initial parameters are set (e.g., for treatment, for imaging) in accordance with an exemplary embodiment of the invention, for example, frequency, energy intensity, duty cycle, pulse duration, pulse repetition frequency, duration of treatment, focused and/or unfocused mode, maximum temperature for element 102. In an exemplary embodiment of the invention, the initial parameters are set according to a treatment plan, for example, as described with reference to co-filed PCT application "Tissue Treatment" (PCT Patent Application No. PCT/IB2011/054640 filed on Oct. 18, 2011), incorporated herein by reference in its entirety. Optionally, the treatment plan is based on clear anatomical landmarks, such as arterial bifurcations.

At 1500, catheter 1222 in inserted into the body of a patient, in accordance with an exemplary embodiment of the invention. Standard vascular access methods can be used, for example, from the femoral artery. Optionally, catheter 1222 is threaded using a guidewire 1202 (e.g., standard 0.014 over the wire, rapid exchange) to the target treatment site (e.g., an artery such as the iliac, renal, carotid, aorta) under image guidance, such as fluoroscopy. Alternatively or additionally, catheter 1222 is directed inside a guiding sheath to the anatomical treatment location.

In an exemplary embodiment of the invention, the initial parameters are set manually (e.g., by a user) using an interface coupled to a controller. Alternatively or additionally, parameters are automatically determined, such as by a software module of the controller.

In an exemplary embodiment of the invention, catheter 1222 comprises at least one transducer 300, positioned for example, on the side, such as inside a window cut into the catheter shaft 1230. Alternatively, a support for transducer 300 is "U" shaped.

At 1502, contact between an acoustic element 102 of transducer 300 and a surface and/or a wall 1226 of a vessel, cavity and/or lumen is reduced and/or prevented, for example, by a separation element and/or device 1204, in accordance with an exemplary embodiment of the invention. Device 1204 maintains a distance 1218 between element 102 and wall 1226 of at least 1 mm. In an exemplary embodiment of the invention, maintaining at least distance 1218 reduces or prevents overheating of element 102. Optionally, a fluid located in distance 1218 transfers heat away from element 102.

Additional details about separation element 1204 are discussed with reference to co-filed PCT application "Separation Device for Ultrasound Element" (PCT Patent Application No. PCT/IB2011/054638 filed on Oct. 18, 2011), incorporated herein by reference in its entirety.

At 1510, electrical energy is applied to transducer 300, for example, according to parameters set at 1506, in accordance with an exemplary embodiment of the invention.

In an exemplary embodiment of the invention, target tissue 1216 is treated by an ultrasound beam 1228 from transducer 300. In some embodiments, treating comprises a thermal effect (e.g., heating to above 55 degrees Celsius) and/or a cavitation effect. In some embodiments, damage and/or treatment to tissues (e.g., normal, healthy) surrounding target tissue 1216 is reduced and/or prevented. In some embodiments, treatment and/or damage to a volume of tissue between target tissue 1216 and wall 1226 is reduced and/or prevented. Selectively targeting tissue is discussed in more detail with reference to PCT application "Tissue Treatment" (PCT Patent Application No. PCT/IB2011/054640 filed on Oct. 18, 2011).

Optionally, at 1504, one or more variables are measured and/or estimated as part of treatment feedback, for example, a flow rate of blood 1220 inside the vessel (e.g., using transducer 300 in Doppler mode), a temperature of transducer 300 (e.g., using sensor 308), distance 1218 (e.g., using acoustic feedback), distance 1232 (e.g., using transducer 300 in imaging mode), and/or impedance of transducer 300 (e.g., electrical measurements), in accordance with an exemplary embodiment of the invention.

In some embodiments, variables measured at 1504 are used to calibrate and/or adjust parameters at 1506, for example, by a look-up table of correlated values. Optionally, measurements as in 1504 occur during and/or after the treatment. Optionally or additionally, adjustment of parameters as in 1506 occurs during and/or after the treatment.

Optionally, at 1508, the integrity of transducer 300 is verified, for example, for mechanical failure and/or presence of foreign matter (e.g., thrombus), in accordance with an exemplary embodiment of the invention. Integrity is verified, for example, by measuring changes in the impedance of transducer 300. Optionally, verification of integrity occurs during and/or after treatment.

Measuring the integrity of transducer 300 is described in more detail with reference to co-filed PCT application "An Ultrasound Transceiver and uses thereof" (PCT Patent Application No. PCT/IB2011/054636 filed on Oct. 18, 2011), incorporated herein by reference in its entirety.

Optionally, at 1516, transducer 300 is used in an imaging mode to obtain feedback about a target tissue 1216. One or more non-limiting examples of target tissues 1216 include, fat, nerves, vasa vasora, lymph, tumor, connective tissue, plaque (e.g., atherosclerotic). Target tissue 1216 may be located a distance 1232 away from the inner surface of wall 1226. Examples of the maximum distance 1232 of target tissue 1216 that can be imaged using transducer 300 include 0.5 mm, 1 mm, 2 mm, 5 mm, 10 mm, or other smaller, intermediate or larger distances. Alternatively or additionally, one or more non-limiting examples of ultrasound imaging methods to estimate the extent of thermal damage in the target tissue and/or surrounding tissue include, measuring the ultrasound backscatter coefficient, ultrasound elastography, measuring US absorption and/or scattering from the treatment region, spectral signature mapping, classification according to a classification matrix of tissues, and/or the ultrasonic effect.

Optionally, at 1512, element 102 is cooled, in accordance with an exemplary embodiment of the invention. Optionally, cooling occurs by transfer of heat from element 102 to a surrounding fluid such as blood 1220, saline, urine, water, angiography contrast fluids, cerebrospinal fluid, lymph, mucous, stomach acid. Alternatively or additionally, cooling occurs by injection of a cooled volume of a liquid (e.g., saline, radio-opaque dye) through tube 1206, and/or circulation of a liquid through tube 1208. Alternatively or additionally, cooling is increased using active heat flux, such as the thermoelectric cooler.

In some embodiments, cooling of element 102 is controlled by the controller, using feedback obtained about the temperature of element 102, for example, from sensor 308.

Additional details about cooling element 102 are discussed with reference to co-filed PCT application "An Ultrasound Transceiver and cooling thereof" (PCT Patent Application No. PCT/IB2011/054641 filed on Oct. 18, 2011), incorporated herein by reference in its entirety.

Optionally, at 1514, one or more of 1504, 1516, 1508, 1510 and/or 1512 are repeated, for example, in a feedback cycle.

Bubble Transducer

Element

Figure 3A:
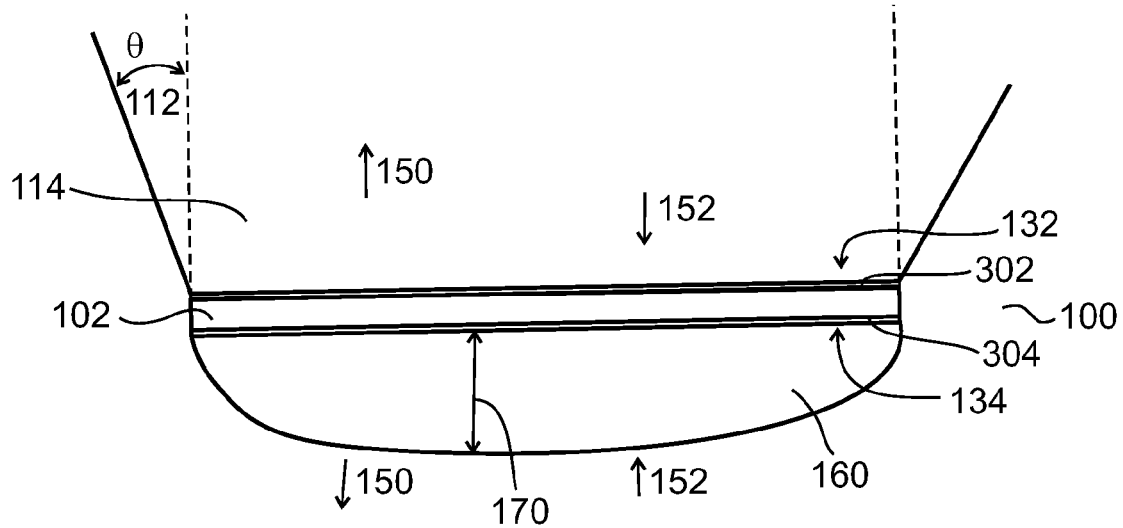
FIGS. 3A-B are views of an ultrasound transducer coupled to a bubble, in accordance with an exemplary embodiment of the invention.
Figure 3B:
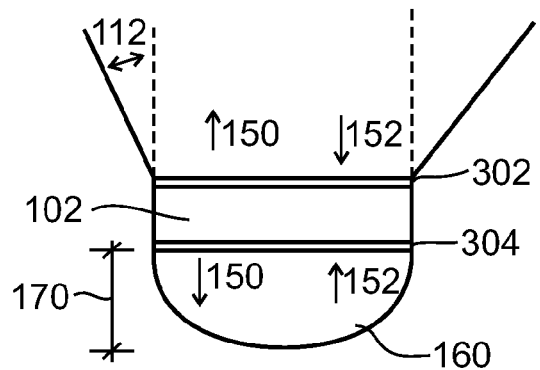

Referring now to the drawings, FIGS. 3A-B illustrate an ultrasound transducer 100 (e.g., ultrasound emission element) for medical therapy, in accordance with an exemplary embodiment of the invention. FIG. 3A is a side view, and FIG. 3B is a cross sectional view of transducer 100. Transducer 100 is designed for high intensity output, for example, up to 100 watts per square centimeters, to cause tissue damage (e.g., heating), while being sufficiently small, for example, about 10 mm (length)×about 1.5 mm (width)×about 0.8 mm (thickness), to be inserted inside blood vessels of the human body on a catheter.

In an exemplary embodiment of the invention, an element 102 is adapted to produce and/or transmit a beam 114 of ultrasound energy. Without being bound to theory, a rectangular element 102 produces an ultrasound beam with relatively low divergence when vibrating, (e.g., for simplification, expansion (arrows 150) and/or contraction (arrows 152)) in response to a sinusoidal voltage applied between a first surface 132 and a second surface 134.

In an exemplary embodiment of the invention, element 102 is vibrated to produced a beam 114 intensity of at least 1-10 watts/cm$^2$, 20 watts/cm$^2$, 30 watts/cm$^2$, 50 watts/cm$^2$, 100 watts/cm$^2$ or other smaller, intermediate or larger intensities.

In an exemplary embodiment of the invention, at least two electrodes 302 and/or 304 are configured to apply a voltage across at least some volume of the element 102, for example, electrode 302 is located on at least some surface 132 and/or electrode 304 is located on at least some surface 134.

In an exemplary embodiment of the invention, electrodes 302 and/or 304 are made out of an electrically conductive biocompatible material such as fired silver. Optionally, electrodes 302 and/or 304 are relatively thin, for example, 5-10 micrometers, or other smaller, intermediate or larger thicknesses. Optionally, electrodes 302 and/or 304 are coupled to element 102 by a process such as a firing process.

In an exemplary embodiment of the invention, element 102 is made out of a material suitable to produce ultrasound energy, for example, a piezo-electric such as lead zirconate titanate (PZT), for example, piezo-electric quartz and/or ceramic.

In an exemplary embodiment of the invention, the thickness of element 102 (e.g. space between electrodes 302 and 304) is about 50 micrometers, about 100 micrometers, about 200 micrometers, about 400 micrometers, or other smaller, intermediate or larger thicknesses are used.

In an exemplary embodiment of the invention, the voltage applied causes element 102 to be vibrated at a frequency, for example, of about 5 Mhz, about 10 Mhz, about 20 Mhz, about 50 Mhz, about 60 Mhz, or other smaller, intermediate or larger frequencies are used.

In an exemplary embodiment of the invention, the thickness of element 102 is related to the expected frequency of vibration of element 102, optionally linearly related, for example, a thickness of 100 micrometers for a frequency of 20 Mhz, a thickness of 200 micrometers for a frequency of 10 Mhz.

In an exemplary embodiment of the invention, the shape of element 102 is rectangular. Alternatively, element 102 is square. Alternatively, other shapes are used, for example, one or more of, annular, semi-annular, concave. Alternatively or additionally, element 102 is flat with an array of electrodes. Alternatively or additionally, an array of elements 102 is used. Alternatively or additionally, several elements 102 are used, wherein elements 102 are spaced apart and/or angled apart. Alternatively or additionally, element 102 produces an ultrasound beam in two opposite directions simultaneously, for example, if the bubble is not used.

In an exemplary embodiment of the invention, element 102 is planar.

In an exemplary embodiment of the invention, element 102 is relatively long, for example, having a length of about 1 mm, about 2 mm, about 4 mm, about 6 mm, about 8 mm, about 10 mm, or other smaller, intermediate or larger lengths are used.

In an exemplary embodiment of the invention, the width of element 102 is relatively short, for example, about 0.2 mm, about 0.6 mm, about 1.0 mm, about 1.4 mm, about 2.0 mm, or other smaller, intermediate or larger widths are used.

In an exemplary embodiment of the invention, beam 114 is unfocused, for example, beam does not converged at a point, for example, beam diverges relatively little. Alternatively, beam 114 is focused, for example, as described with reference to FIG. 12C.

In an exemplary embodiment of the invention, beam 114 produced by the rectangular element 102 is relatively straight, spreading an angle 112 of about fifteen (15) degrees relative to a normal to surface 132 of element 102, when measured along the length. Non-limiting ranges of angle 112 include about 0.1 degrees to about 30 degrees. Without being bound to theory, angle 112 is inversely related to surface 132 and/or inversely related to the frequency of vibration of element 102 (e.g., smaller element 102 and/or lower frequency increase angle 112).

A potential advantage of a relatively thin element 102 vibrating at a relatively high frequency is the reduction and/or prevention of the risk of mechanical failure (e.g., breaking, fracturing). Inventors hypothesize that the high frequency vibration and/or a relatively thin height results in a rate of heat transfer from element 102 (e.g., to a surrounding fluid), that is sufficient to prevent and/or reduce damage to element 102 due to heat buildup.

In an exemplary embodiment of the invention, transducer 100 has a resonance and an anti-resonance. Optionally, transducer 100 has several resonant frequencies and several anti-resonances formed from local maxima, such as on an efficiency graph. Optionally, transducer 100 is used at a working frequency equal to the anti-resonance. The anti-resonance was found empirically to provide a relatively higher efficiency in terms of a ratio of conversion of electrical energy to sound, as opposed to conversion of electrical energy to heat.

In an exemplary embodiment of the invention, element 102 uses different anti-resonance values for the working frequency when available. For example one anti-resonance may be used for moderate heating of the tissue, another for power heating of the tissue and yet another for monitoring.

In some embodiments, element 102 is used to receive ultrasound energy, for example, returning echoes, such as during imaging of tissues. Receiving ultrasound energy can create a voltage across electrodes 302 and/or 304. Optionally, emission element 102 can function both as an emitter and receiver, for example, as a transceiver. Emission element 102 and/or a catheter may be provided with an acoustic/ultrasonic transducer.

In an exemplary embodiment of the invention, ultrasound emission element 102 is an unfocused emission element. For example, the beam produced by element 102 does not focus and/or converge at a point. For example, the beam produced by element 102 stays substantially straight and/or slightly diverges (e.g., about 15 degrees) after leaving element 102. Optionally, element 102 is a widebeam emission element, for example, the beam produced by element 102 diverges more than about 15 degrees after leaving element 102.

Bubble Transducer

Gas Bubble

In an exemplary embodiment of the invention, at least one gas bubble 160 is coupled to at least some area of a side element 102, for example, to side 134, such as to electrode 134. In an exemplary embodiment of the invention, bubble 160 relatively increases the efficiency of element 102 in converting electrical power to acoustic energy.

In an exemplary embodiment of the invention, the gas in bubble 160 is room air. Alternatively, the gas in bubble 160 is for example, one or more of, oxygen, nitrogen, carbon dioxide, carbon tetrafluoride.

In an exemplary embodiment of the invention, bubble 160 is formed by surface tension of a liquid (e.g., water, saline, blood) around the gas, such as during immersion of element 102 into the liquid.

In an exemplary embodiment of the invention, a thickness 170 of bubble 160 (e.g. measured approximately in the center) is about 1 micrometer, 10 micrometers, about 50 micrometers, about 100 micrometers, about 200 micrometers, or other smaller, intermediate or larger thicknesses are used. In an exemplary embodiment of the invention, bubble 160 is about the size of surface area of side 134 of element 102.

In an exemplary embodiment of the invention, bubble 160 prevents an ultrasound beam from passing through. Bubble 160 can be used to create ultrasound beam 114 from one direction of element, for example, from surface 132.

Figure 4A:
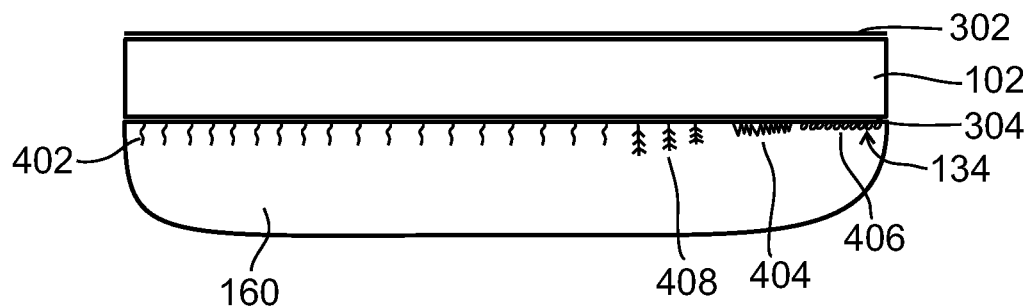
FIGS. 4A-F are illustrations of some embodiments to couple the bubble to the acoustic element, in accordance with some embodiments of the invention.

As illustrated in FIG. 4A, in accordance with some embodiments of the invention, the surface area of side 134 is increased to relatively increase the coupling force between bubble 160 and side 134. One or more examples of increasing the surface area of side 134 include, hair-like projections 402, jagged surface variations 404, microspheres 406 and/or tree like projections 408.

Figure 4B:
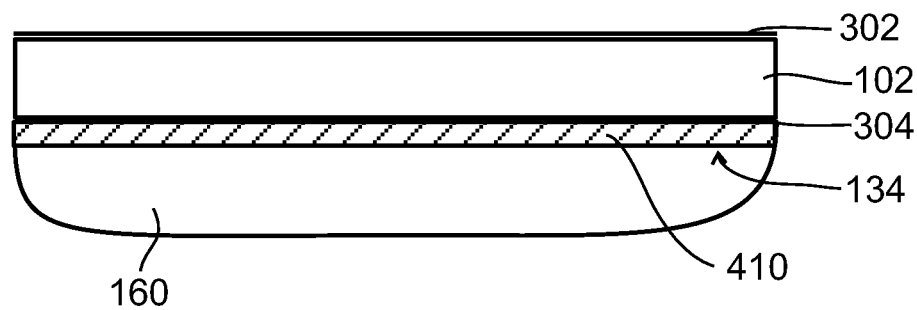

As illustrated in FIG. 4B, in accordance with some embodiments of the invention, a coating 410 on at least a portion of side 134 is used to relatively increase the coupling force between bubble 160 and side 134. Optionally coating 410 is hydrophobic. Alternatively or additionally, coating is hydrophilic. One or more non-limiting examples of coating 410 include, Parylene available from Para Tech Coating Inc., Galxyl available from GALENTIS. In some embodiments, coating 410 is applied for example, by chemical vapor deposition. In some embodiments coating 410 is relatively thin, for example, 5 micrometers.

Figure 4C:
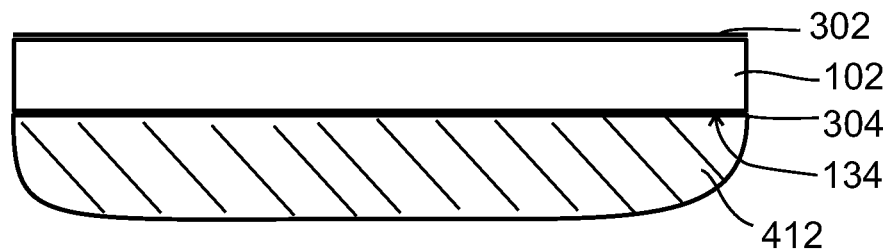

As illustrated in FIG. 4C, in accordance with some embodiments of the invention, bubble 160 is formed before immersion of element 102 into the liquid, for example, from a liquid film 412 such as microbubbles in an acoustic ultrasound contrast agent, for example, as described with reference to FIG. 7B.

Figure 4D:
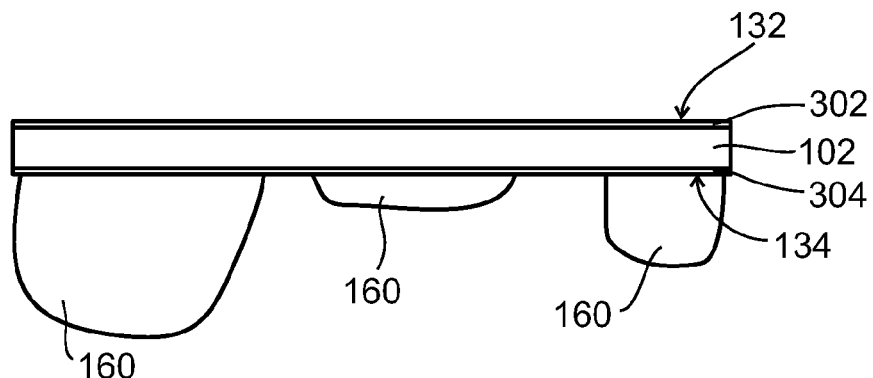

As illustrated in FIG. 4D, in some embodiments of the invention, two or more bubbles 160 are coupled to side 134 of element 102.

Figure 4E:
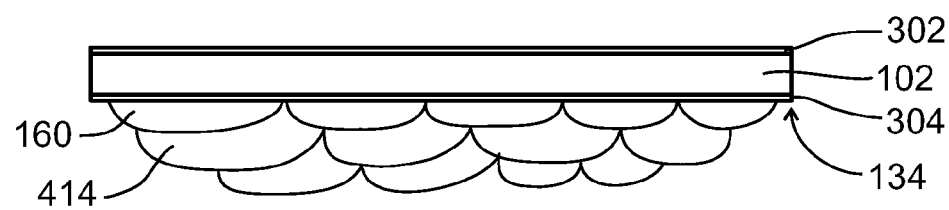

As illustrated in FIG. 4E, in some embodiments of the invention, a second bubble 414 is coupled to one or more bubbles 160 coupled to side 134. Optionally second bubble 414 is coupled, for example, by static and/or surface tension. Optionally, there is a space between bubbles. In some embodiments of the invention, two or more bubbles 414 are used to create bubble shapes to relatively increase the efficiency of element 102, for example, the vibration of element 102 can be mathematically modeled, with two or more bubbles 414 designed accordingly.

Figure 4F:

As illustrated in FIG. 4F, in an exemplary embodiment of the invention, bubble 160 is coupled to side 134 by increasing the surface tension on bubble 160. In an exemplary embodiment of the invention, a base 450 creates a space 452 between base 450 and side 134, thereby increasing the surface tension. Optionally, base 450 is coated with a coating 454 to relatively increase the surface tension, for example coating like 410. One or more non-limiting examples of base 450 will be discussed in more detail below, such as board 104 and/or housing 800.

In some embodiments of the invention, bubbles 160 and/or 414 are of one or more sizes. Alternatively or additionally, bubbles 160 and/or 414 contain one or more types of gases.

In an exemplary embodiment of the invention, bubble 160 is coupled to most or all of area of side 134.

Figure 3C:
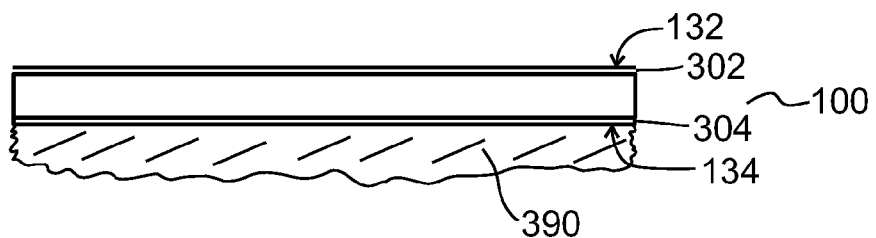
FIG. 3C is a side view of the transducer, with bubble replaced by a material, in accordance with some embodiments of the invention.

FIG. 3C is a side view of transducer 100, with bubble 160 replaced by a material 390, in accordance with some embodiments of the invention. In some embodiments of the invention, material 390 has an effect similar to bubble 160, for example, relatively increasing the efficiency of transducer 100. Optionally, material 390 is a foam like material filled with the gas. Alternatively or additionally, material 390 is a heat conductive, electrically isolating polymeric pad.

Experimental Results Showing Some Potential Advantages

Inventors performed experiments to test a first hypothesis that the presence of the bubble improves the efficiency (e.g., converting electrical energy into ultrasound energy) of a transducer under an intensity setting sufficient for medical therapy, a second hypothesis that the structure of the transducer provides for coupling of the bubble to a side of the transducer, even during the intensity setting sufficient for medical therapy, and a third hypothesis that the structure of the transducer (e.g., relatively thin) reduces and/or eliminates the risk of mechanical failure of the transducer under the intensity setting sufficient for medical therapy.

Inventors performed five experiments, in which they immersed one of the five transducers in water to form a bubble. An intensity setting sufficient to perform a medical treatment procedure was applied to the transducer, for example, as described with reference to 1510 in FIG. 2. The efficiency of the transducer was measured using a hydrophone to measure the acoustic intensity output, and/or 'off the shelf' instruments to measure the applied electrical power. The results showed a surprisingly high efficiency (e.g., conversion of applied electrical power to ultrasound energy), for example, up to 60%.

Subsequently, inventors increased the intensity to a relatively high level, higher than would be required for the medical treatment procedure.

As shown in the table below, the results show a decrease in efficiency at the relatively higher intensity relative to the efficiency measured at the relatively lower intensity. The differences in efficiencies are statistically significant, having p value<0.01 for all 5 experiments.

After removing the transducers and drying them at room temperature in room air for 12 hours, the transducers were re-immersed in the water, and the efficiency under the intensity level sufficient to perform a medical procedure was re-measured as shown in the table below. The transducers used in the experiment are based on FIGS. 4F, 5M and 5N, having a coating of Parylene applied by chemical vapor deposition. The bubble is retained by surface tension, for example, in a containment area (e.g., the depression in the board).

| Transducer # | Efficiency under an intensity level sufficient for medical treatment (set 1) | Efficiency under a higher intensity than required for medical treatment (set 2) | Efficiency after 12 hours of drying and sufficient intensity for medical treatment (set 3) |
|---|---|---|---|
| A | 43% | 36.4% | 40% |
| B | 56% | 40.7% | 56% |
| C | 60% | 49.6% | 60% |
| D | 54% | 39.0% | 55% |
| E | 60% | 49.3% | 61% |

Surprisingly, the results showed that the efficiency of all 5 transducers after drying (set 3) was approximately equivalent to the first set of efficiency measurements (set 1).

As a control, before removing transducer D from the water for drying, transducer D was left for 12 hours in the water. The efficiency after 12 hours in the water remained at 39%.

Without being bound to theory, inventors believe that the results can be explained by the presence of the bubble during the first set of measurements, followed by the escape of the bubble during the second set of measurements, followed by the reformation of the bubble during the third set.

Inventors believe that the surprising results of a higher efficiency at the first set of measurements, relative to the second set, is due to the presence of the bubble.

Inventors believe that the surprising results of a higher efficiency at the first set of measurements, relative to the second set, support the hypothesis that the bubble remains coupled to the element, even under the intensity and/or the frequency sufficient for medical therapy.

Inventors believe that the surprising results of an increase in efficiency after drying the transducers (set 3), to about the same level as the first set of measurements, support the hypothesis that mechanical failure of the transducer is reduced and/or prevented, even under a higher intensity level than is required for medical therapy.

In summary, in accordance with the first hypothesis, the experimental results support the theory that the bubble significantly improves the efficiency of the transducer. In accordance with the second hypothesis, the experimental results support the theory that the bubble remains coupled to the transducer during an intensity and/or a frequency setting sufficient for medical therapy, even though the element is vibrating. In accordance with the third hypothesis, the experimental results support the theory that the structure of the transducer reduces and/or eliminates the risk of mechanical failure during the intensity setting sufficient for medical therapy.

Additional Potential Advantages of Some Embodiments

A potential advantage of the relatively high efficiency (e.g., 60%) of transducer 100 is a relatively low rate of heat transferred to the blood, potentially preventing and/or reducing the risk of adverse events such as thrombus formation.

A potential advantage of the relatively small surface area 132 of element 102 and/or a relatively straight bream 114 and/or a relatively high energy output intensity is that focusing of beam 114 is not required, for example, to target and/or treat tissues.

One or more potential advantages of the non-focused ultrasonic beam include:
- A relatively large treatment volume cross-section as a result of the size of the transducer face (as compared to focused ultrasound that provides for a relatively smaller treatment volume).
- A relatively even spread of ultrasonic energy in the cross section of the beam. No need for precise positioning from the wall of the blood vessel or from the target tissue like in focused ultrasound.

Method of Making the Transducer

Figure 7A:
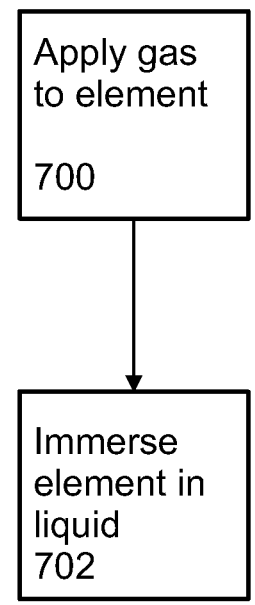
FIGS. 7A-B are block diagrams of methods of making a transducer, in accordance with an exemplary embodiment of the invention.
Figure 7B:
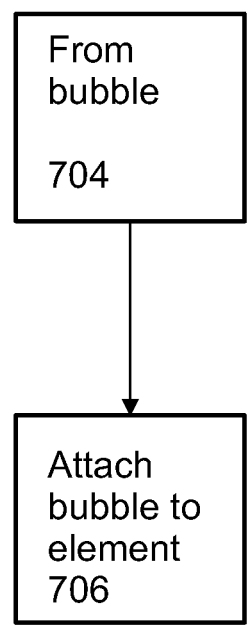

FIGS. 7A-B illustrate some exemplary methods of making the ultrasound transducer (e.g., transducer 100), in accordance with an exemplary embodiment of the invention.

FIG. 7A illustrates a method coupling and/or forming bubble 160 during submersion of element 102 into a liquid, in accordance with an exemplary embodiment of the invention.

At 700, gas (e.g., room air, nitrogen, oxygen, carbon dioxide) is applied to element 102, such as to side 134, for example, by immersing element 102 and/or side 134 in the gas, in accordance with an exemplary embodiment of the invention.

At 702, element 102 is immersed in the liquid (e.g., blood, saline), such as during a medical procedure, in accordance with an exemplary embodiment of the invention. In an exemplary embodiment of the invention, bubble 160 is formed and/or coupled to element 102, for example, by surface tension and/or by methods as described with reference to FIGS. 4A and/or 4B.

FIG. 7B illustrates a method of coupling an exiting and/or formed bubble 160 to element 102, in accordance with some embodiments of the invention.

At 704, bubble 160 is formed and/or obtained, for example, from a liquid such as microbubbles in an acoustic ultrasound contrast agent in accordance with some embodiments of the invention.

At 706, bubble 160 is coupled to element 102, for example, as described with reference to FIG. 4C.

Supported Element

Figure 5A:
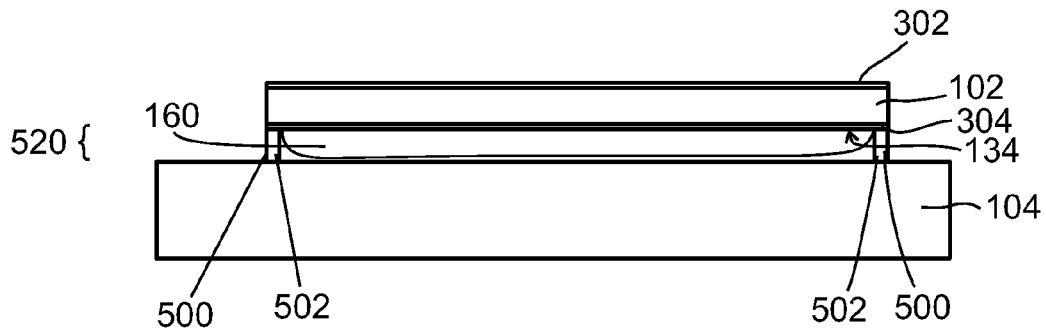
FIGS. 5A-P are illustrations of some embodiments of the ultrasound transducer coupled to the bubble suspended over a board, in accordance with some embodiments of the invention.
Figure 5B:
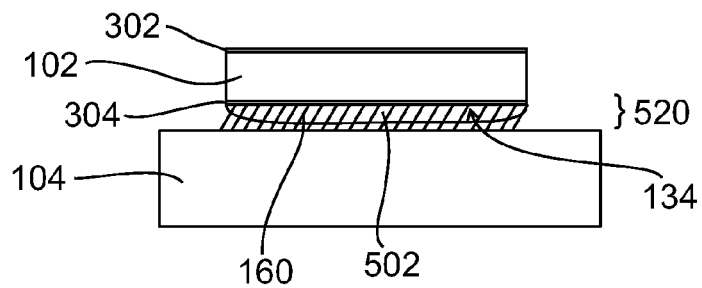
Figure 5C:
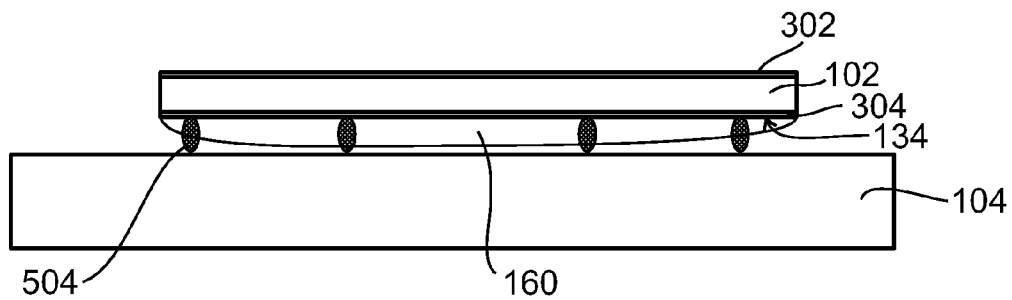
Figure 5D:
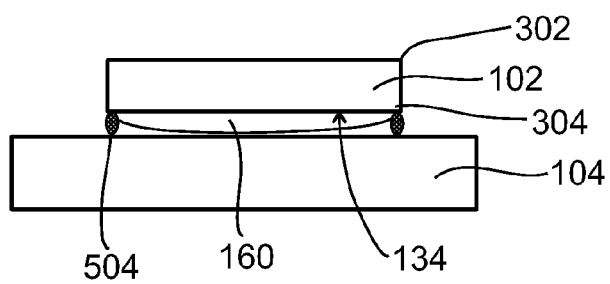
Figure 5E:
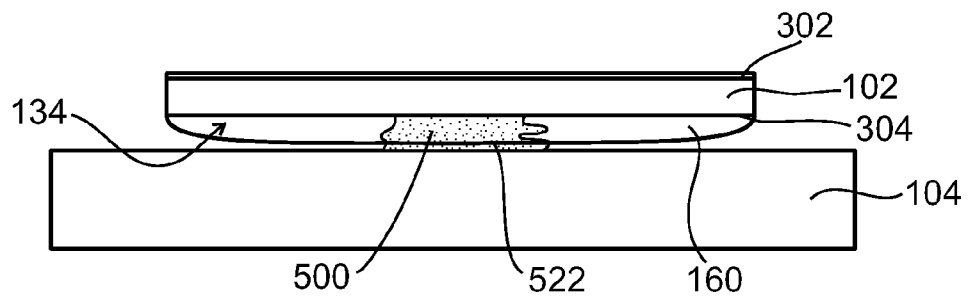
Figure 5F:
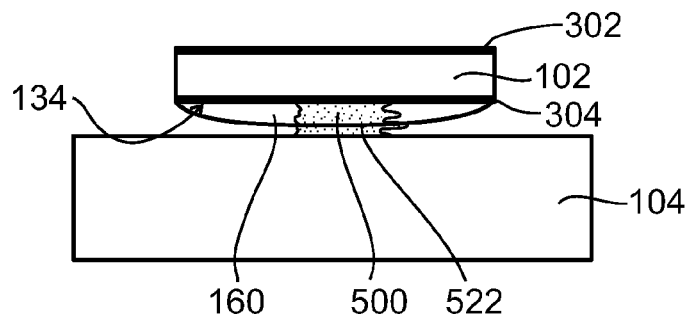
Figure 5G:
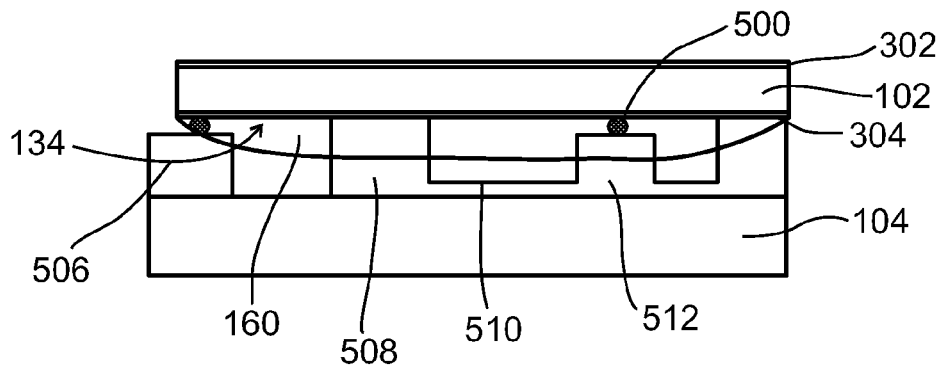
Figure 5H:
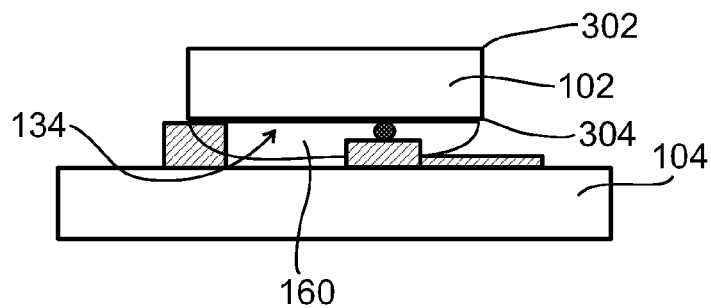
Figure 5I:
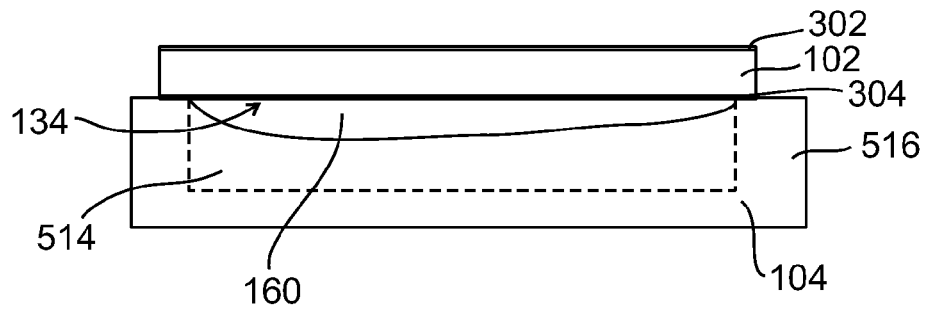
Figure 5J:
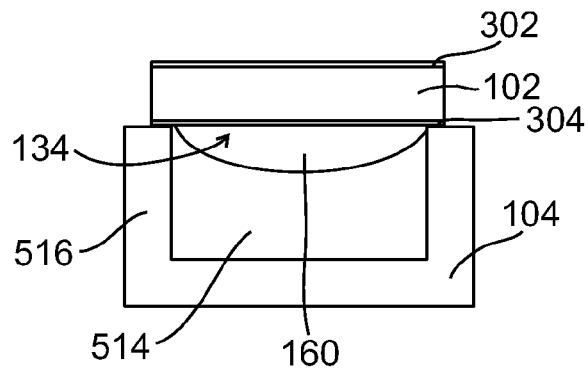
Figure 5K:
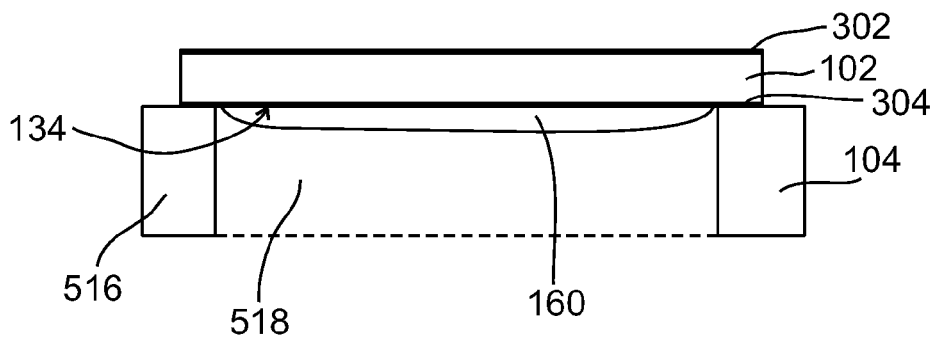
Figure 5L:
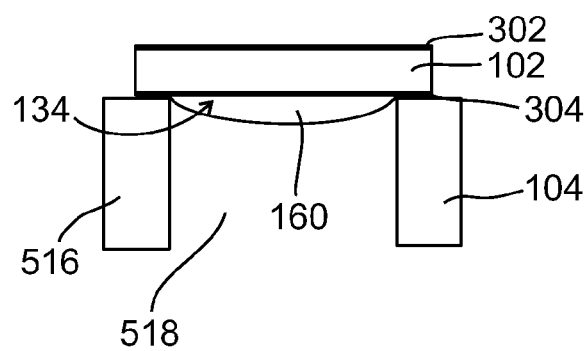
Figure 5M:
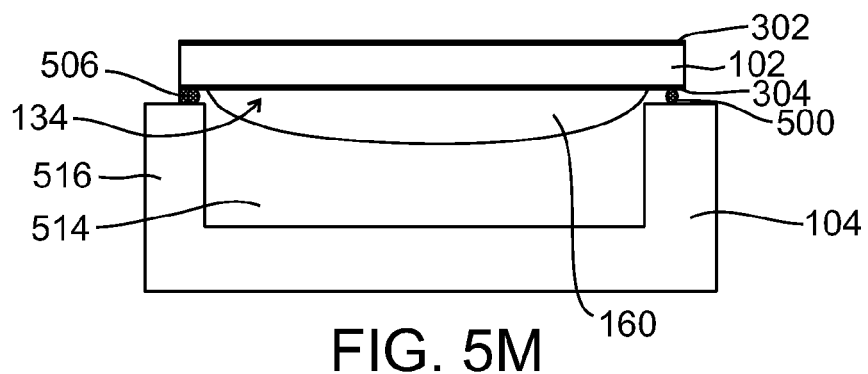
Figure 5N:
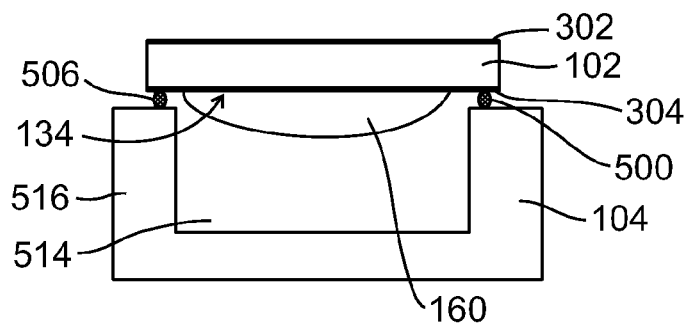
Figure 5O:
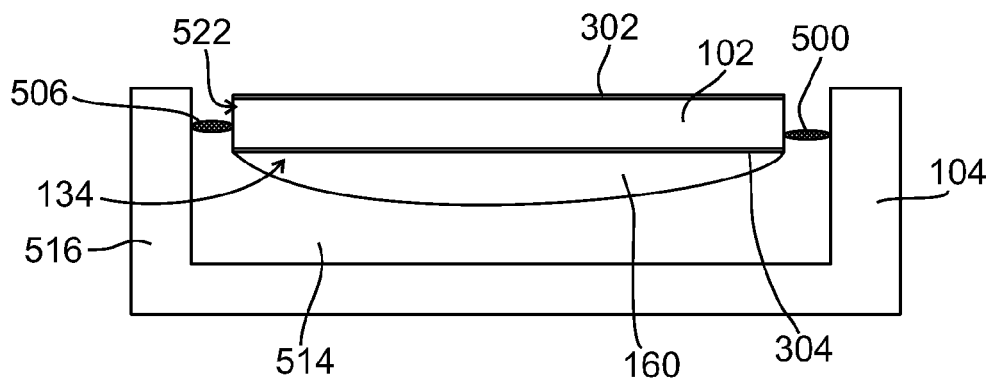
Figure 5P:
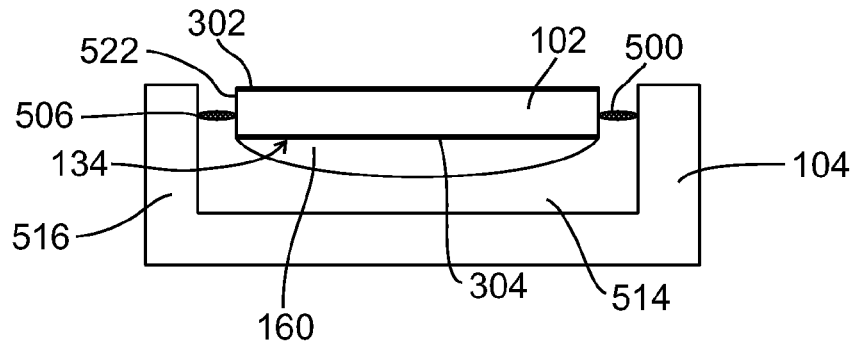

FIGS. 5A-P illustrate some exemplary embodiments of the invention, wherein a transducer (e.g., element 102, with at least two electrodes 302 and/or 304, optionally with bubble 160 coupled to side 134), is supported above at least some area of a support board 104. Optionally, element 102 is suspended over at least some volume of a depression 514 and/or an aperture 518 of the board 104. In an exemplary embodiment of the invention, at least one region and/or area of element 102 is used to suspend element 102.

In an exemplary embodiment of the invention, board 104 is a printed circuit board.

In an exemplary embodiment of the invention, at least some part of board 104 (e.g. part supporting element 102) is made from a rigid material, for example, one or more of, a hard polymer, glass-fiber, carbon fiber. Alternatively or additionally, at least some part of board 104 is made from a flexible material, such as polyimide.

In an exemplary embodiment of the invention, the shape of board 104 is for example, rectangular. Non-limiting examples of dimensions of a rectangular board 104 are 10×1.5 mm, with a uniform thickness of 150 micrometers.

In an exemplary embodiment of the invention, a relatively small surface area of element 102 (e.g., side 134) is used to couple element 102 to board 104, for example, about 0.06%-about 17% of the surface area of the element, for example, one location (e.g., drop) is about 0.06% of the surface area, eight locations are about 0.5% of the surface area of side 134.

In an exemplary embodiment of the invention, element 102 is suspended a distance 520 above board 104, for example, 0.1 micrometers, 1 micrometers, 10 micrometers, 17 micrometers, 100 micrometers, 150 micrometers, 200 micrometers, or other smaller, intermediate or larger distances. Optionally, the bubble is located in the space formed by distance 520. Optionally, the size of the bubble is determined according to distance 520.

FIG. 5A-5F illustrate a material 500 to suspend element 102 above board 104, in accordance with an exemplary embodiment of the invention. In an exemplary embodiment of the invention, material 500 suspends element 102 above board 104 at 1 coupling area, 2 coupling areas, 4 coupling areas, 8 coupling areas, 12 coupling areas, or other smaller, intermediate or larger numbers of coupling areas. In an exemplary embodiment of the invention, material 500 is for example, one or more of, glue, wire solder, paste solder. In an exemplary embodiment of the invention, the shape of material 500 is for example, one or more of, irregular (e.g., a blob) 522, a sphere 504, a strip 502. Optionally, material 500 is electrically conductive, for example, electrically coupled to electrode 302 and/or 304. Alternatively or additionally, material 500 is thermally conductive.

FIG. 5A is a side view, and FIG. 5B is a cross sectional view of material 500 arranged along the periphery of the width of element 102, for example, as strip 502, in accordance with some embodiments of the invention. Illustrated is the non-limiting example of 2 materials 500 arranged as strips 502 along both widths.

FIG. 5C is a side view, and FIG. 5D is a cross sectional view of material 500 arranged along the periphery of the length of element 102, for example, as sphere 504, in accordance with some embodiments of the invention. Illustrated is the non-limiting example of 8 materials 500 arranged as spheres 504 along both lengths.

FIG. 5E is a side view, and FIG. 5F is a cross sectional view of material 500 arranged away from the periphery of element 102 (e.g., centrally located). Illustrated is the non-limiting example of the use of one material 500, having irregular shape (e.g., blob) 522.

FIG. 5G is a side view, and FIG. 5H is a cross sectional view of a material, for example, a metal such as copper 506, used to suspend element 102 above board 104, in accordance with some embodiments of the invention. Optionally, copper 506 is printed on board 104, for example, using standard printed circuit board techniques. In some embodiments, a relatively thicker layer 508 of copper 506 is used to suspend element 102, for example, a thickness of 50-200 micrometers. Optionally, a relatively thinner layer 510, for example, 1-150 micrometers of copper 506 is used, for example, to conduct electricity and/or heat. Alternatively or additionally, a relatively medium thickness layer 512 (e.g., thickness between thick layer 508 and thin layer 510) is used to suspend element 102, for example with material 500 bridging the remaining gap.

In an exemplary embodiment of the invention, copper 506 is located on the surface of board 104 according to function, for example, to support element 102 and/or to conduct electricity and/or heat. Optionally, copper 506 coats at least some area of board 104.

In an exemplary embodiment of the invention, embodiments according to FIGS. 5A-H are selected in part according to electrification and/or cooling requirements, for example, relatively more contact areas provide relatively increased electrical power and/or cooling.

A potential advantage of relatively few contact areas as in FIGS. 5A-H is reducing damping forces on element 102.

FIG. 5I is a side view and FIG. 5J is a cross sectional view, of element 102 suspended over at least some volume of a depression 514 in board 104, in accordance with some embodiments of the invention.

FIG. 5K is a side view, and FIG. 5L is a cross sectional view of element 102 suspended over at least some volume of an aperture 518 in board 104, in accordance with some embodiments of the invention. Optionally, element 102 is suspended over at least some volume of depression 514 and/or aperture 518 by walls 516 of board 104 forming depression 514 and/or aperture 518, for example, at least at two areas, such as at the periphery of width of element 102 and/or at least at one area, such as away from the periphery (e.g., centrally).

In an exemplary embodiment of the invention, embodiments according to FIGS. 5I-L are selected according to the size of the bubble.

FIG. 5M is a side view and FIG. 5N is a cross sectional view, of material 500 suspending element 102 over at least some volume of a depression 514 in board 104, in accordance with some embodiments of the invention.

FIG. 5O is a side view and FIG. 5P is a cross sectional view, of material 500 suspending at least some volume of element 102 inside at least some volume of depression 514. Optionally, material 500 couples a side 522 (e.g., along width) of element 102 to the inside wall 516 of depression 514.

In an exemplary embodiment of the invention, embodiments according to FIGS. 5M-5P are selected according to bubble size, electrification requirements and/or cooling requirements.

Inventors hypothesize that a potential advantage of a free standing, and/or suspended element 102 is increased efficiency in producing acoustic and/or ultrasound energy. Without being bound to theory, inventors hypothesize that the increased efficiency is a result of a relatively small amount of resistance and/or damping of element 102, for example, as a result of the relatively small surface area of side 134 used to couple element 102 to board 104.

Board Features

Figure 6A:
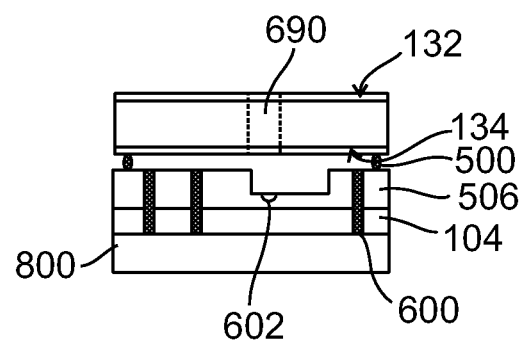
FIGS. 6A-B are illustrations of some possible features on board, in accordance with some embodiments of the invention.
Figure 6B:
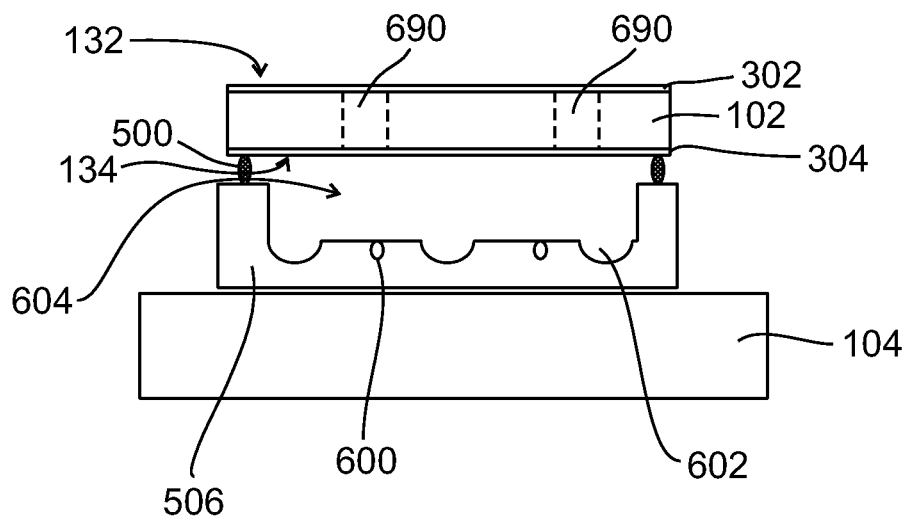

FIG. 6A is a side view, and FIG. 6B is a cross sectional view illustrating some possible features on board 104 to control heat removal and/or control flow 604 of a liquid (e.g., blood, saline, water) under element 102, in accordance with some embodiments of the invention. Optionally, element 102 comprises one or more holes 690, such as from side 132 to side 134. Optionally, holes 690 allow for flow 604 of the liquid between sides 132 and 134.

In some embodiments of the invention, heat conductivity away from element 102, such as to board 104 is controlled, for example, by thermal conductive elements such as gold and/or copper filled holes 600. In some embodiments, holes 600 are thermally coupled to element 102, for example, through material 500 and/or copper 506. Other non-limiting examples of heat sinks to which holes 600 can conduct heat from element 102 to, include a heat sink (e.g., housing 800 as will be described below), a thermoelectric cooler, flowing liquid 604 (e.g., blood, water, saline, dye).

In some embodiments of the invention, the total surface area of holes 600 facing element 102 is relatively larger than the total surface area of material 500 contacting element 102.

In some embodiments of the invention, one or more flow channels 602 control flow 604 of the liquid, for example, between element 102 and board 104. Optionally, element 102 is not coupled to bubble 160. Optionally, flow channels are grooves on the surface of board 104, for example, shaped by copper 506.

A potential advantage of controlling flow 604 under element 102 is to reduce and/or prevent the formation of thrombus due to stagnation of blood. Another potential advantage is to increase the rate of heat removal from element 102 to the flowing liquid 604 (e.g., blood, water, saline, dye).

Housing

Figure 8A:
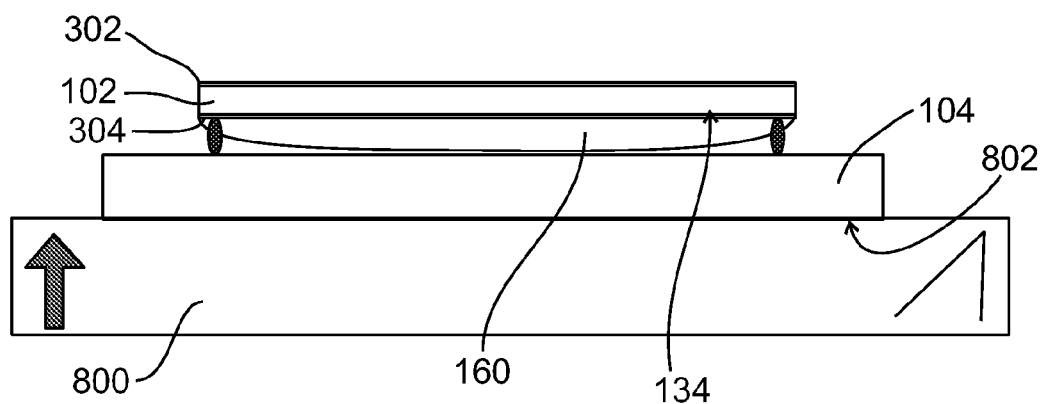
FIGS. 8A-B are illustrations of a housing used with the transducer, in accordance with some embodiments of the invention.
Figure 8B:
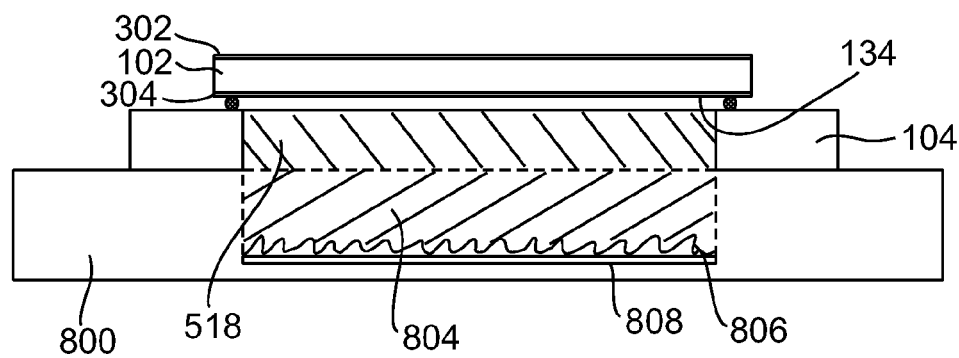

FIGS. 8A-B illustrate the use of a housing 800 coupled board 104, in accordance with some embodiments of the invention. In some embodiments, housing 800 provides one or more functions, for example, mechanical support, radio-opacity, acoustic damping, acoustic reflection, focusing.

In some embodiments of the invention, housing 800 is coupled to catheter 1222, for example, at least some part of catheter 1222 has housing 800.

In some embodiments of the invention, housing 800 is coupled to board 104, for example, to side 802 of board (e.g., side not coupled to element 102). One or more examples of methods to couple housing 800 to board 104 include gluing, welding, crimping, screws.

In some embodiments of the invention, housing 800 provides mechanical support to board 104 and/or element 102, for example, by being made out of a rigid material such as steel, stainless steel, ceramics, hard polymers, carbon fiber. Optionally at least some of housing 800 is a Peltier element.

In some embodiments, housing 800 acts as a heat sink to increase the rate and/or amount of heat removed from element 102, for example, by being thermally coupled to element 102 through board 104 (e.g., through material 500 and/or copper 506 and/or holes 600).

In some embodiments, housing 800 contains radio-opaque direction markers such as an arrow 804 and/or an angle 806 (e.g., 45 degrees) to assist in orienting element 102 under fluoroscopic image guidance.

In some embodiments, housing 800 comprises a depression 804 and/or aperture, optionally in continuity with aperture 518 in board 104. Optionally, a bubble resides inside depression 804 and/or aperture 518. In some embodiments, at least some of element 102 is positioned over at least some volume of depression 804. Optionally, depression 804 dampens the acoustic energy transmitted by side 134 of element 102, for example, in some embodiment wherein element 102 is not coupled to bubble 160. One or more examples of methods to cause damping include, filling at least some of the volume of depression 804 with a damping material such as tungsten, irregular surface variations 806 (e.g., jagged edges) to randomly reflect acoustic energy from side 134. Alternatively or additionally, depression 804 reflects ultrasound, for example, by a flat reflecting surface 808, such as steel. Alternatively or additionally, depression 804 focuses ultrasound energy, for example, by a concave reflecting surface.

A potential advantage of housing 800 is to relatively increase the ability of element 102 to perform imaging, for example, by damping vibrations so that element 102 can receive returning echoes. Another potential advantage of housing 800 is to focus the ultrasound energy.

Multielement Transducers

FIGS. 9A-9D illustrate some exemplary embodiments of a multielement transducer (e.g., two or more elements), in accordance with an exemplary embodiment of the invention.

Figure 9A:
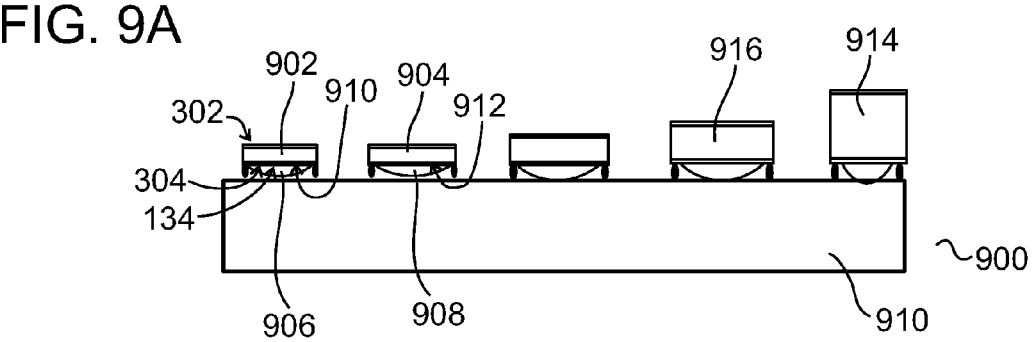
FIGS. 9A-D are illustrations of some embodiments of a multielement transducer, in accordance with some embodiments of the invention.

FIG. 9A illustrates a multielement transducer 900, wherein a side 910 of at least one element 902 is coupled to at least one bubble 906, in accordance with an exemplary embodiment of the invention. Optionally, a second side 912 of a second element 904 is coupled to at least one second bubble 908. Alternatively, second element 904 is not coupled to bubble 908.

Figure 9B:
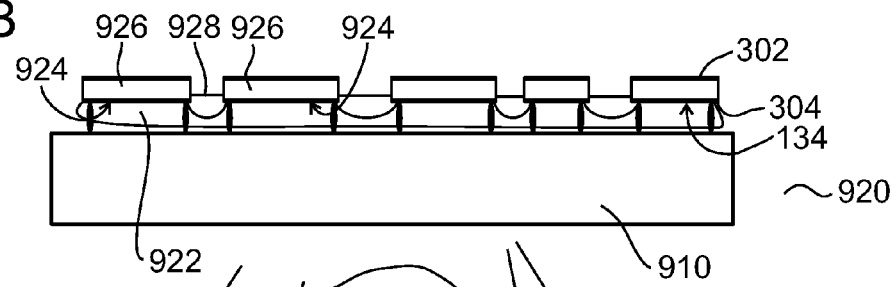

FIG. 9B illustrates a multielement transducer 920, wherein a bubble 922 is coupled to at least two sides 924 of at least two elements 926, in accordance with some embodiments of the invention. Optionally, elements 926 are connected by one or more connectors 928, wherein connector 928 is coupled to bubble 922.

Figure 9C:
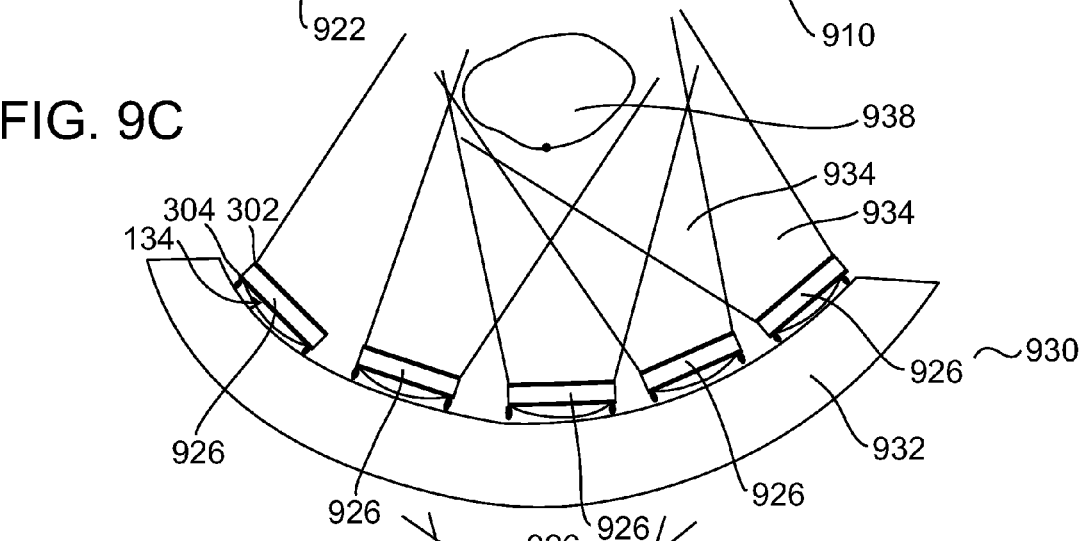

FIG. 9C illustrates a multielement transducer 930 designed to focus at least two ultrasound beams 934 from at least two elements 926 at a focal area and/or volume 938 (e.g., tissue), in accordance with some embodiments of the invention. Optionally, board 932 is shaped (e.g., concave) to result in focal area and/or volume 938.

Figure 9D:
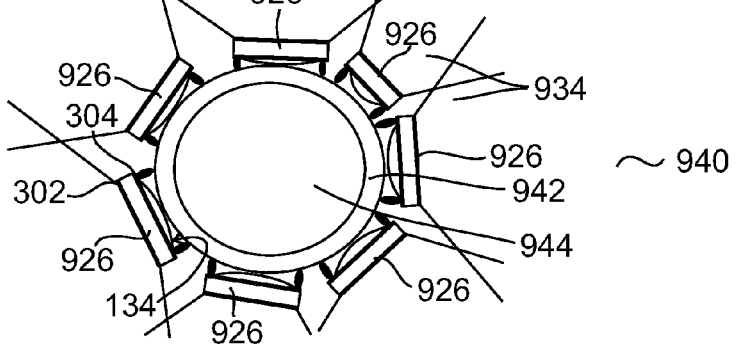

FIG. 9D illustrates a multielement transducer 940, designed to direct one or more ultrasound beams 934 over a relatively wide area, in accordance with some embodiments of the invention. Optionally, beams 934 cover a cross sectional area and/or volume of 360 degrees, for example, to provide treatment (e.g., damage by heat and/or mechanic effect) of a cross section of a blood vessel. Alternatively, beams 934 cover a cross sectional area and/or volume of less than 360 degrees. In some embodiments, board 942 is shaped to result in the coverage of beams 934, for example, having a cross sectional shape of a circle (e.g., ring) and/or semi-circle (e.g., arc). Optionally, board 942 contains a lumen 944.

In some embodiments, elements of transducers 900 920 930 and/or 940 are suspended over a support board 910 932 and/or 942.

In some embodiments of the invention, elements described with reference to FIGS. 9A-9D perform one or more functions, for example, imaging and/or treatment. Optionally, one or more elements are made out of one or more materials, for example, according to the function and/or application. For example, one or more elements designed for treatment are made out of a high intensity PZT formulation such as Navy Type III (available from Morgan Matroc as PZT-8). For example, one or more elements designed for imaging are made out of a PZT formulation designed for sensing such as Navy Type II (available from Morgan Matroc as PZT-5A). Alternatively or additionally, one or more elements are designed with one or more variations in dimensions, for example, according to the function and/or application. Alternatively or additionally, elements are individually controllable, for example, through a switch. For example, element 914 is made out of PZT NAVY TYPE III, and/or has a thickness of 200 micrometers, and/or is controlled to produce ultrasound at a frequency of 10 Mhz, and/or is used for treatment such as damage by heating. For example, element 916 is made out of PZT Navy Type II, and/or has a thickness of 100 micrometers, and/or is used for imaging by being controlled to produce ultrasound at a frequency of 20 Mhz, and/or controlled to receive the reflected echoes.

In some embodiments of the inventions, two or more elements are controlled to act as a phased array, for example, to direct the ultrasound beam and/or increase the intensity of the ultrasound beam at one or more locations.

Multiregional Transducer

Figure 10:
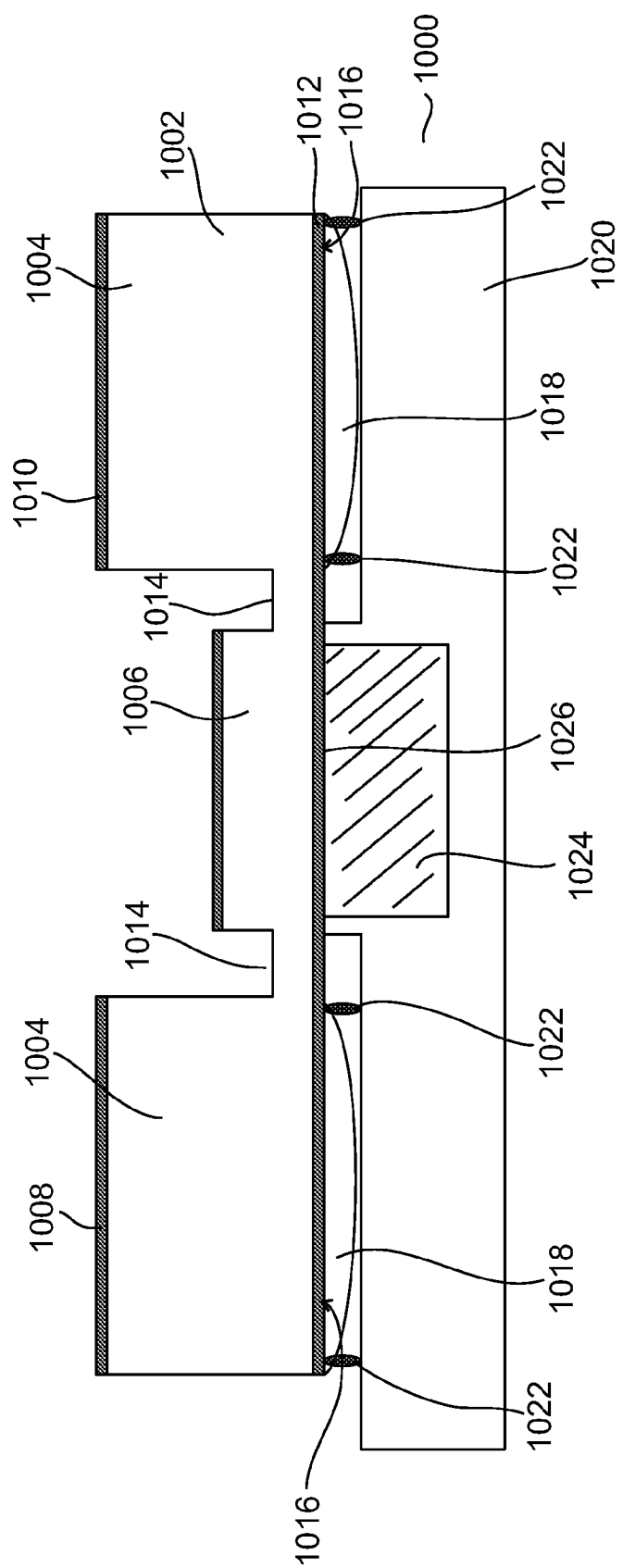
FIG. 10 is an illustration of an exemplary design of a multiregional transducer, in accordance with some embodiments of the invention.

FIG. 10 is an illustration of an exemplary design of a multiregional transducer 1000 to perform two or more functions, for example, acoustic feedback (e.g., imaging) and/or treatment, in accordance with some embodiments of the invention.

In some embodiments of the invention, element 1002 comprises two or more regions, for example, one or more regions 1004 for producing ultrasound energy for treatment and/or one or more regions 1006 for producing ultrasound energy for imaging. In some embodiments, one or more imaging regions 1006 receive returning ultrasound echoes. Optionally, the echoes are processed (e.g., by a controller) to provide imaging data, such as of target tissues.

In some embodiments of the invention, element 102 is positioned over at least some area of a board 1020.

In some embodiments, regions 1004 and/or 1006 are separated by an inert region 1014, for example, a region of element 1002 that does not have a voltage applied across (e.g., one or zero electrodes across the inert region).

In some embodiments, electrodes at least on one side of regions with the same function (e.g., treatment regions 1004 and/or imaging regions 1006) are electrically coupled to function at substantially the same time under the same control, for example, electrodes 1008 and/or 1010 of treatment regions 1004 are electrically coupled. Optionally, regions with different functions (e.g., 1004 and/or 1006) share a common electrode 1012 on an opposite side (e.g., sides 1016 and/or 1026).

In some embodiments, region 1004 is designed for treatment (e.g., damage to tissue by heat), for example, by producing relatively higher intensity ultrasound energy. Optionally, the thickness of region 1004 is related to the expected frequency of the produced ultrasound energy, for example, 200 micrometers for 10 Mhz. Alternatively or additionally, side 1016 of region 1004 is coupled to at least one bubble 1018. Alternatively or additionally, region 1004 is suspended over board 1020, for example, by materials 1022 (e.g., glue, solder, copper).

In some embodiments, two or more regions (e.g., at two or more different location) configured for treatment are designed to operate at two or more different frequencies, for example, region 1004 on the left side of FIG. 10 can be designed to treat at 10 Mhz, and/or region 1004 on the right side of FIG. 10 can be designed to treat at 20 Mhz. Alternatively or additionally, two or more regions are electrified separately (e.g., have separate electrodes), for example, region 1004 on the left at a sinusoidal pattern of 10 Mhz and/or region on the right at 20 Mhz.

In an exemplary embodiment of the invention, two or more regions have different resonance frequencies. Alternatively, at least some of the resonance frequencies are the same.

In some embodiments of the inventions, two or more regions are controlled to act as a phased array, for example, to direct the ultrasound beam and/or increase the intensity of the ultrasound beam at one or more locations.

In some embodiments, region 1006 is designed for acoustic feedback (e.g., imaging), for example, for producing ultrasound energy and/or receiving the returning echo. Optionally, the thickness of region 1006 is related to the expected frequency of the produced ultrasound energy, for example, 100 micrometers for 20 Mhz. Alternatively or additionally, at least some area of side 1026 of region 1006 is coupled to at least some volume and/or area of a depression 1024 in board 1020, optionally containing a damping material such as tungsten.

In some embodiments of the invention, the ultrasound beam produced by imaging regions 1004 and the ultrasound beam produced by treatment region 1006 substantially overlap.

A potential advantage of transducer 1000 is the ability to perform imaging and/or treatment without having to reposition and/or reorient transducer 1000.

Cover

Figure 11A:
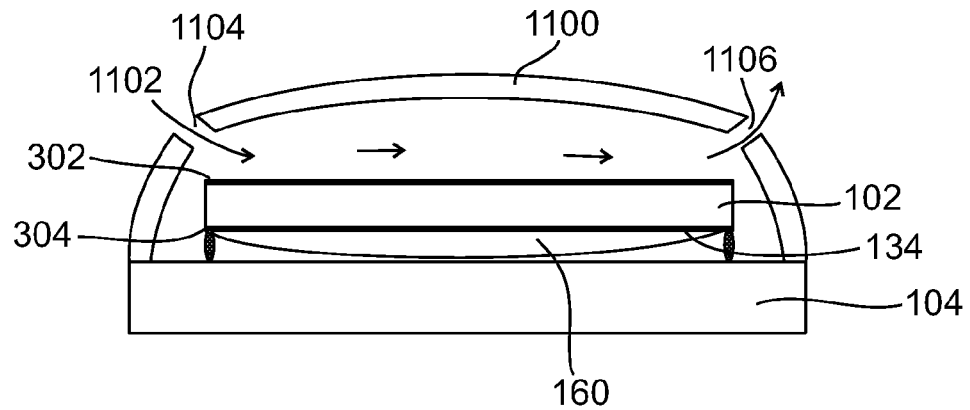
FIGS. 11A-C are illustrations of some embodiments of a transducer with a canopy, in accordance with some embodiments of the invention.
Figure 11B:
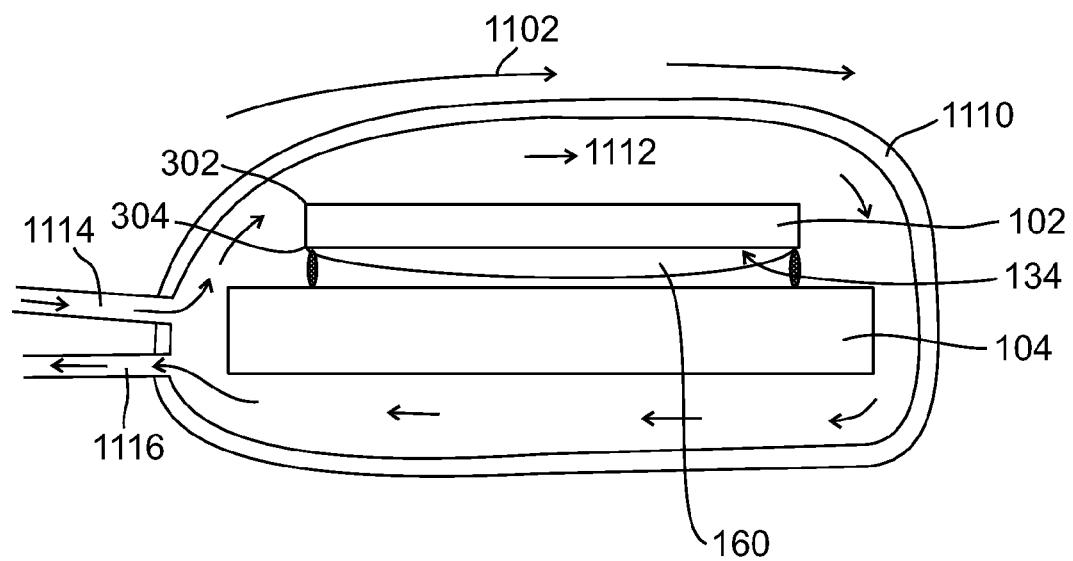
Figure 11C:
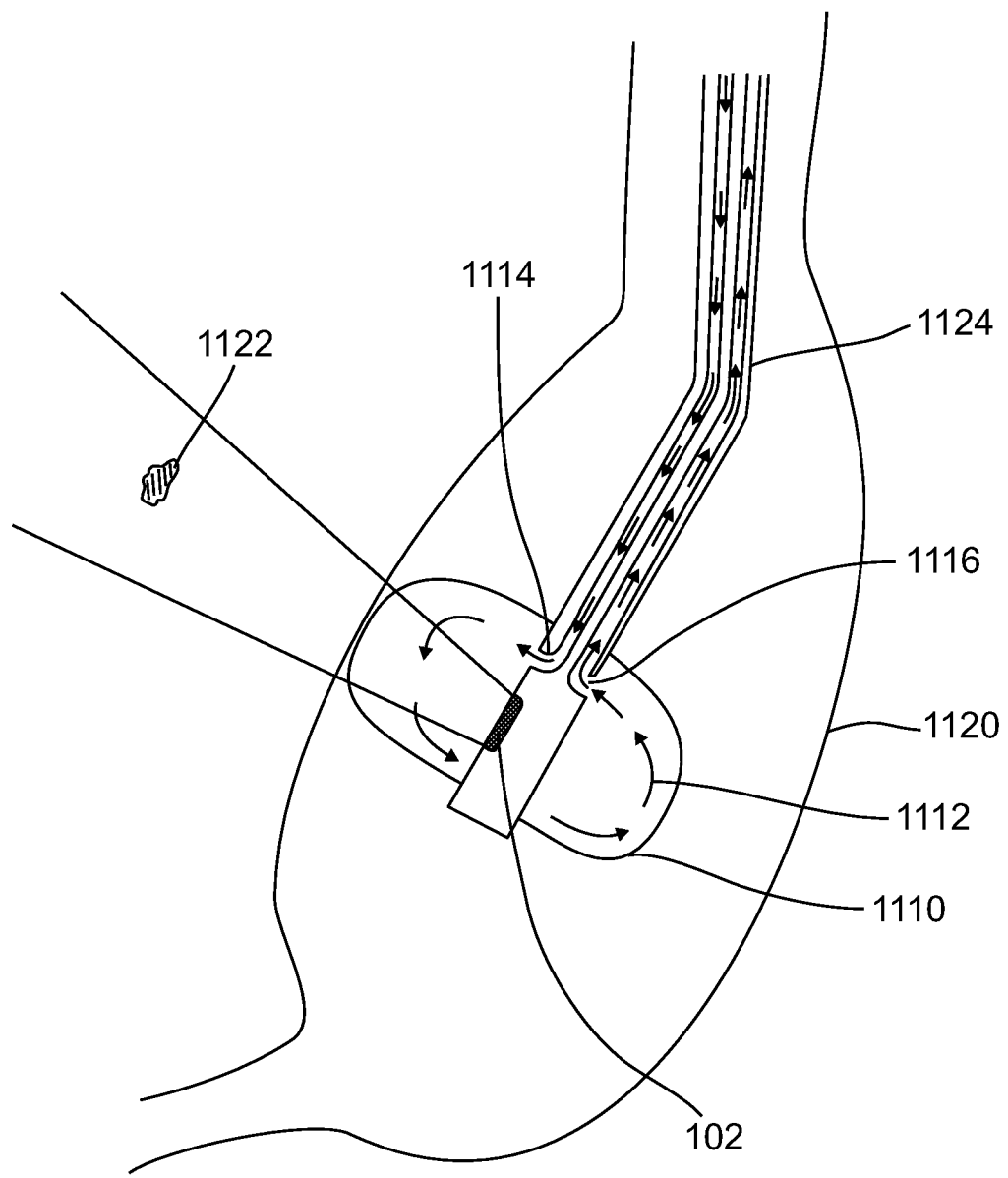

FIGS. 11A-C illustrate a canopy and/or cover for the transducer, in accordance with some embodiments of the invention.

FIG. 11A illustrates a canopy 1100 for the transducer that provides for an external fluid 1102 (e.g., blood) to circulate between element 102 and canopy 1100, in accordance with some embodiments of the invention. Optionally, external fluid 1102 enters through one or more apertures 1104 in canopy 1100 and exits through one or more apertures 1106 in canopy 1100. In some embodiments, canopy 1100 is permeable to ultrasound energy, for example, made out of polyester, polyimides, polyolefins, latex, PeBax, nylon, silicon, PTFE. Optionally, canopy 1100 does not affect the ultrasound beam (e.g., direction, spread). Alternatively, canopy 1100 is shaped and/or designed to affect the ultrasound beam, for example, diverge the beam and/or filter the beam (e.g., the first harmonic), such as a lattice made out of metal having a spacing of about half a wavelength of the ultrasound beam that will affect the target tissue.

FIG. 11B illustrates a canopy 1110 for the transducer that isolates transducer from an external fluid 1102 (e.g., blood), in accordance with some embodiments of the invention. Optionally, canopy 1110 is a balloon, for example, made out of a material such as latex, PeBax, nylon, silicon, PTFE. In some embodiments, an internal fluid 1112 (e.g., saline, water, radio-opaque dye) occupies the volume between element 102 and canopy 1100. Optionally, fluid 1112 circulates between element 102 and canopy 1100, for example, from an inlet port 1114 to an outlet port 1116.

A potential advantage of canopy 1100 and/or 1110 is to provide for fluid 1102 and/or 1112 to circulate in order to remove heat generated by element 102 during function (e.g., vibration). Another potential advantage is to protect the transducer and/or element 102 from mechanical damage, for example, inadvertent contact with foreign objects. Another potential advantage is to reduce and/or prevent the formation of thrombus on the surface of transducer, for example, if the circulating fluid 1112 is not blood.

FIG. 11C illustrates the use of an embodiment of the transducer, for example as shown in FIG. 11B, as part of a catheter 1124 and/or endoscope, to treat tissues 1122 in body orifices and/or cavities that do not naturally contain a sufficient amount of an in-situ fluid that can bridge a distance between element 102 and tissues, for example, stomach 1120. The ultrasound beam 1126 produced by element 102 travels through fluid 1112, then through canopy 1110 into the tissues lining stomach 1120 to reach target tissue 1122.

In some embodiments, the transducer as shown in FIG. 11C is used to treat tissues from outside of the body, for example, through the skin and/or through an incision in the skin.

In some embodiments, the cover is used to focus the ultrasound beam, for example, to treat a target tissue.

Exemplary Element Shapes

Figure 12A:
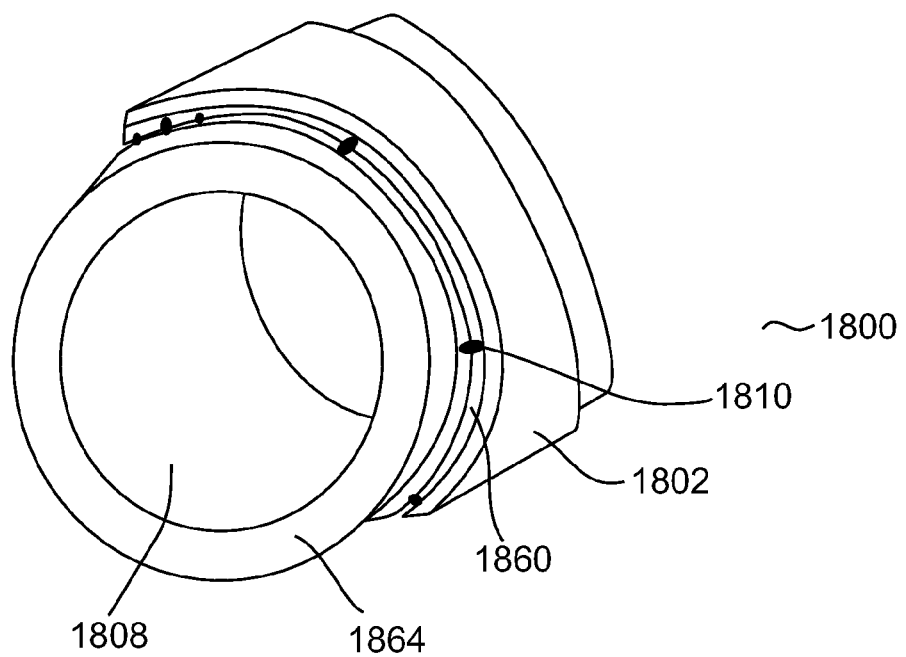
FIGS. 12A-C are illustrations of some embodiments of transducer shapes, in accordance with some embodiments of the invention.
Figure 12B:
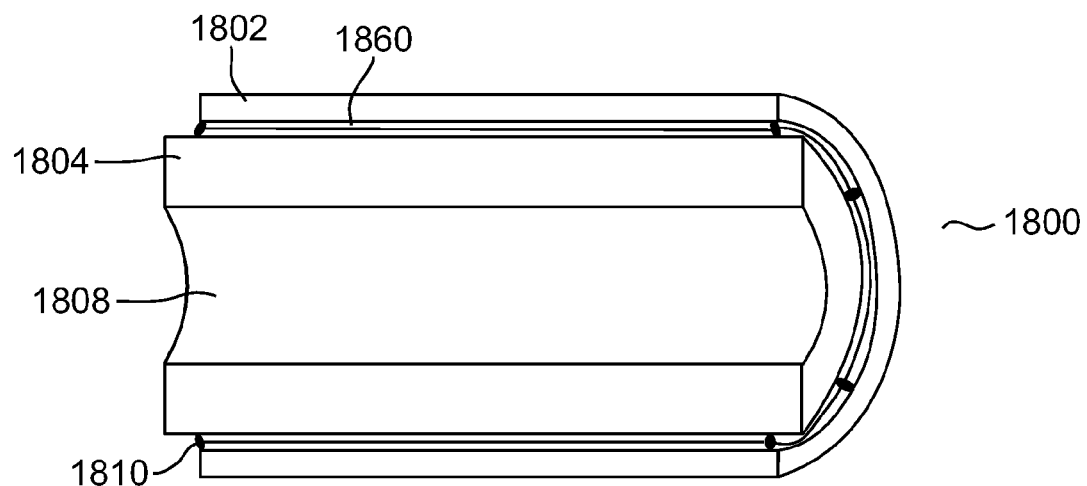

FIG. 12A is a front view, and FIG. 12B is a cross sectional view (e.g., along the long axis) of a transducer 1800 with an annular and/or ring cross section (e.g., element 1802, bubble 1860 and/or board 1804 have an annular and/or ring cross section), in accordance with some embodiments of the invention. Alternatively, transducer 1800 (e.g., element 1802, bubble 1860 and/or board 1804) is semi-annular and/or arc shaped, for example, having an arc length of less than 360 degrees. Optionally, transducer 1800 contains a lumen 1808. In some embodiments, element 1802 is suspended above board 1804, for example, through a coupling material 1810 (e.g., glue, solder, copper). A potential advantage is treatment of a cross sectional area and/or volume of tissue around a blood vessel.

Figure 12C:
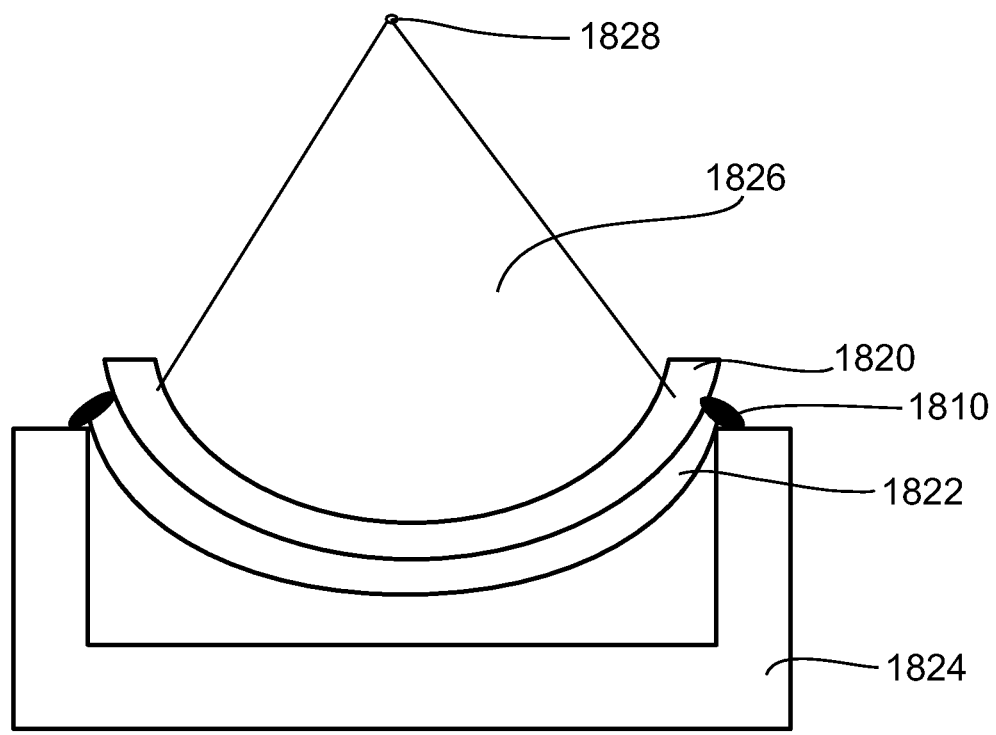

FIG. 12C is a cross sectional view of a transducer with an element 1820 for focusing an ultrasound beam 1826 at a focal point 1828. Optionally, element 1820 has a concave cross section, for example, a slice from a cylinder. Alternatively, element 1820 is concave in shape, for example, a plane sliced from a sphere. In some embodiments the concave shape is selected for a desired focal length. A potential advantage is obtaining relatively high intensity of ultrasound energy at the focal point.

Catheter

Exemplary Design

Referring back to FIG. 1, in an exemplary embodiment of the invention, catheter 1222 is small enough to fit into blood vessels for treatment. Exemplary non-limiting sizes of catheter 1222 are 5 French, 7 French, 9 French, 11 French, 15 French, 21 French, or other smaller, intermediate or larger sizes.

In an exemplary embodiment of the invention, non-limiting examples of the size of the acoustic element are about 6 mm (length)×about 1 mm (width)×about 0.2 mm (thickness). Optionally, the length and/or width of the board are relatively larger than those of the element, non-limiting examples of dimensions include, about 10.5 mm (length)×about 1.5 mm (width)×about 0.15 mm (thickness). Optionally or additionally, the width of the housing is relatively similar to that of the element, in some embodiments, the length is slightly shorter, non-limiting examples of dimensions include, about 8.5 mm (length)×about 1.5 mm (width)×about 0.5 mm (thickness). The described dimensions are non-limiting, and other smaller, intermediate or larger sizes can be used.

In an exemplary embodiment of the invention, catheter 1222 comprises one or more lumens containing, for example, one or more of, wires (e.g., twisted pair, such as to measure the temperature using sensor 308), cables (e.g., coaxial cable, such as for delivering electrical power to electrodes 302 and/or 304), cooling elements, tubes for transporting fluid (e.g., saline, coolant, radioopaque dye), guidewire, positioning devices.

Figure 13:
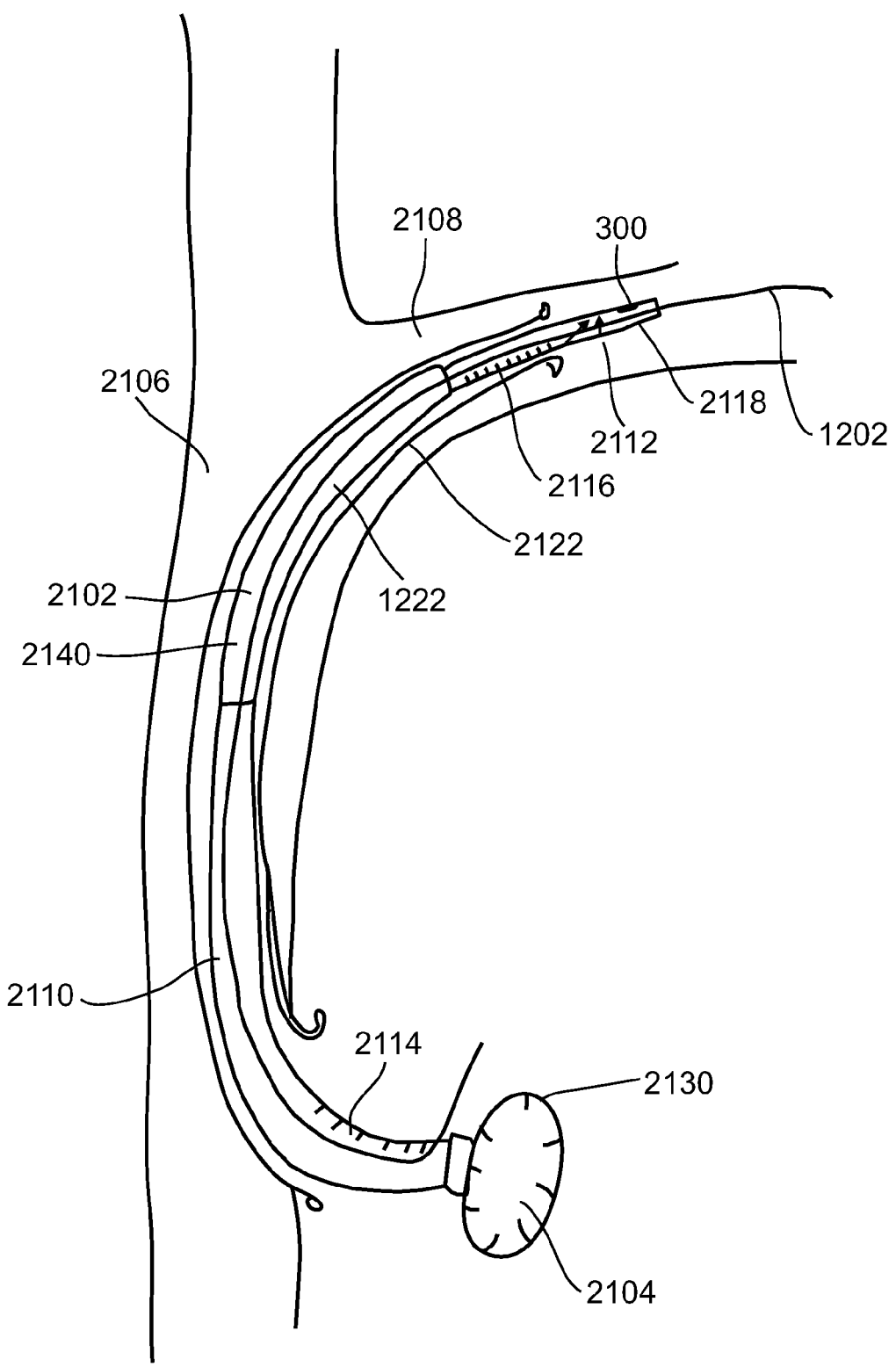
FIG. 13 is an illustration of an exemplary design of a catheter for guiding the transducer inside the body, in accordance with an exemplary embodiment of the invention.

FIG. 13 illustrates an exemplary design of catheter 1222 for guiding transducer 300 into an anatomical body site for medical treatment. Catheter 1222 is shown inside a branch vessel 2108 (e.g., renal, carotid, subclavian) off a main vessel 2106 (e.g., aorta).

In an exemplary embodiment of the invention, catheter 1222 has a relatively small diameter of about 6 Fr, or about 4 Fr, about 8 Fr, or other smaller, intermediate or larger sizes are used.

In some embodiments, an end of catheter 1222 comprising transducer 300 is referred to as 'proximal', an end of catheter 1222 that remains outside the body is referred to as 'distal'.

In an exemplary embodiment of the invention, a catheter shaft 2102 is designed to transmit rotation torque from a rotation controller 2104 to transducer 300, in about a one to one ratio through torturous anatomy (e.g., blood vessel), while reducing and/or preventing kinks. Optionally, a stiff portion 2110 of shaft 2102 is made out of a material sufficiently stiff to transmit torque in an approximately 1:1 ratio, such as a Braided shaft, made of materials such as nitinol, stainless steel and/or Helical Hollow Strand (HSS) available from Fort Wayne Metals and/or Hypotube with laser cutting available from Johnson Matthey Medical and/or polytetrafluoroethylene, nylon, polyurethane, PET, PEEK, ECTFE, ETFE. Optionally, stiff portion is the length of shaft 2102 (e.g., as will be described below) minus the length of catheter tip 2118 (e.g., as will be described below).

In an exemplary embodiment of the invention, catheter tip 2118 of shaft 2102 (e.g., including transducer 300) is made out of a flexible material, for example, one or more materials including, Hypotube with laser cutting available from Johnson Matthey Medical, polytetrafluoroethylene, Nylon, polyurethane, Pebax, Tetrafluoroethylene, Hexafluoropropylene, Vinylidene Fluoride. Optionally, the length of tip 2118 is relatively short, for example, 1 cm, 2 cm, 5 cm, 10 cm, or other smaller, intermediate or larger lengths are used. A potential advantage of a relatively short and/or soft tip 2118 is reducing and/or preventing mechanical damage to the walls of blood vessels as catheter 1222 is moved axially forward and/or rotated. Another potential advantage is the ability to position tip 2118, for example, away from the wall of the blood vessel.

In some embodiments, a central portion 2140 is a continuation of stiff portion 2110. Alternatively, portion 2102 is a continuation of tip 2118. Alternatively, central portion 2140 is designed according to the expected anatomical structure associated with the procedure, for example, having a stiffness other than portion 2110 and/or tip 2118.

In an exemplary embodiment of the invention, a length of catheter 1222, is approximately the length required to reach the treatment site using intravascular routes, for example, 65 cm, 100 cm, 120 cm, 150 cm, or other smaller, intermediate and/or larger lengths. A potential advantage is to reduce the loss of torque and/or to provide for relatively higher shaft 2102 flexibility.

In an exemplary embodiment of the invention, radioopaque markers 2112, located for example on tip 2118, assist in orienting and/or positioning under fluoroscopic guidance. Optionally, markers 2112 are flat. Optionally, markers 2112 show direction, for example, by being arrow shaped. Alternatively or additionally, markers 2112 show degree of rotation, for example, by comparing the angle of the image appearing on x-ray to a 45 (forty-five) degree angle marker 2112.

In an exemplary embodiment of the invention, axial movement markers 2114 indicate the amount of forward and/or reverse motion of catheter 1222. Optionally, markers 2114 are located on a portion of catheter shaft 2102 located outside the body. Alternatively or additionally, markers 2116 are radio-opaque and/or located on tip 2118, for example relatively close to transducer 300, to be visible on fluoroscopic images.

In some embodiments of the invention, the degree of rotation of catheter 1222 (e.g. along the long axis) is shown on controller 2104 by markers 2130.

In some embodiments of the invention, catheter 1222 is directed into position inside an outer sheath 2122. Optionally, sheath 2122 is made out of a material with relatively low friction against catheter 1222, for example, polytetrafluoroethylene (PTFE), polyethylene, polyurethane.

In some embodiments of the invention, catheter 1222 is steerable, even without the guide wire.

In some embodiments of the invention, catheter 1222 is passed through an 8 Fr "hockey-stick" guide catheter. Optionally, other sizes for the guide catheter are available, relative to the size of catheter 1222, for example, about 6 Fr, about 10 Fr, or other smaller, intermediate or larger sizes.

Potential advantages of catheter 1222 include one or more of, precise and/or easy torque following, simple treatment beam directivity feedback and/or control from standard angiographic equipment (e.g. 0, 90, 180, 270 degrees), no need for high operator skills, and/or ability to use contrast agents during treatment.

In some embodiments of the invention, catheter 1222 includes one or more elements to move transducer 300. Optionally, the element is a piezoelectric element that can be vibrated by applying electrical power. Alternatively or additionally, the element moves transducer 300 for relatively fine positioning, for example, an electrically controlled motor. In some embodiments, the element vibrates and/or moves transducer 300 to position the strongest part of the ultrasound beam at the target tissue.

In some embodiments the controller can be calibrated according to the expected intensity profile of the produced ultrasound beam, for example, the controller vibrates and/or moves transducer 300 in order to obtain a desired position for thermally affecting the tissues.

Catheter

Exemplary Positions of Transducer

Figure 14A:
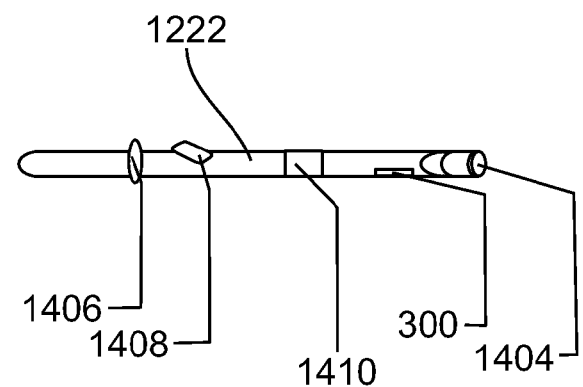
FIGS. 14A-B illustrate some embodiments of possible positions of the transducer on the catheter, in accordance with some embodiments of the invention.
Figure 14B:
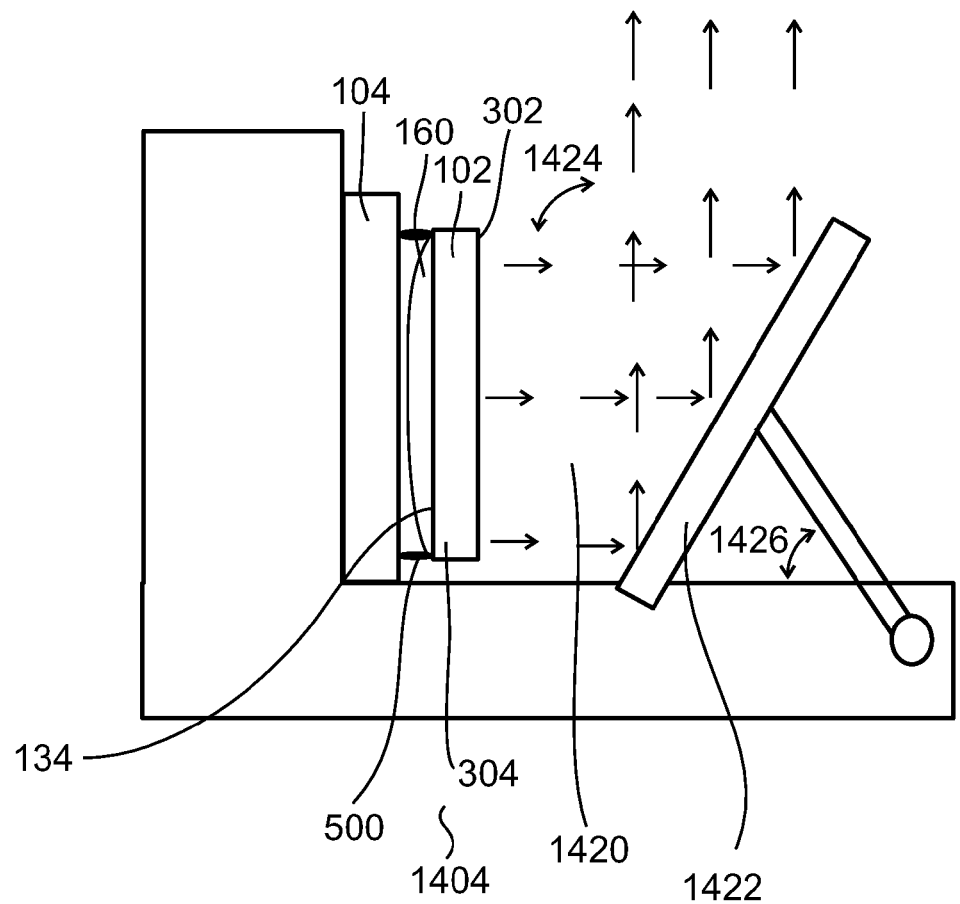

FIG. 14A illustrates one or more possible positions of the transducer on catheter 1222, in accordance with some embodiments of the invention. Optionally, a transducer 300 is positioned at the side of catheter 1222 (e.g., inside a window), for example, as described with reference to FIG. 1. Alternatively or additionally, transducer 1404, for example, as illustrated in FIG. 14B, is positioned at the front of catheter 1222. Alternatively or additionally, a transducer 1408 is placed on an angle, for example, using an angled housing. Alternatively or additionally, an annular or semi-annular transducer 1406, for example, as described with reference to FIGS. 12A-B, is positioned on catheter 1222. Alternatively or additionally, a multielement transducer 1410, for example as described with reference to FIGS. 9A-9D, is positioned on catheter 1222.

There are one or more potential advantages associated with one or more positions of transducer system 300 on catheter 1222. For example, the side position can be easier to orient, control and/or position to target tissues at the periphery of the blood vessel, such as tissues located in the adventitia. For example, the front position may be useful for treating a branch point, where a single vessel splits into two. Another advantage is to send an ultrasound beam towards an object inside the lumen of a vessel (e.g. thrombus). For example, the angular position can be used to target tissues located in areas difficult to target with the side and/or front orientations.

FIG. 14B illustrates a forward facing transducer 1404, in accordance with some embodiments of the invention. Optionally, a reflector 1422 reflects a beam 1420 produced by element 102. Optionally, an angle of reflection 1424 is controllable and/or adjustable (e.g., manually by user, automatically by controller), for example, by adjusting an angle 1426 of reflector 1422. Alternatively, the angle 1424 is preset during manufacturing. A potential advantage is the ability to treat tissue volumes without repositioning the catheter. Another potential advantage is the reduction and/or prevention of the risk of element 102 contacting the vessel wall.

In an exemplary embodiment of the invention, catheter 1222 should not be positioned against the vessel wall, unless element 102 is cooled, for example, using a cooling system as described in the section "CATHETER-OPTIONAL COOLING SYSTEM".

Catheter

Optional Cooling System

Referring back to FIG. 1, a cooling system thermally coupled to element 102 comprises a temperature sensing element, such as sensor 308, to measure and/or estimate the temperature of element 102, and/or a cooling element (e.g., as will be described below) to control and/or maintain the temperature of element 102 (e.g., below a threshold), in accordance with an exemplary embodiment of the invention. One or more examples of sensor 308 include thermocouple, fiber optic temperature sensor, temperature sensing diode, resistance thermometers.

In an exemplary embodiment of the invention, the temperature of element 102 (e.g., as estimated by sensor 308) is controlled to be below about 50 degrees Celsius, about 47 degrees Celsius, about 45 degrees Celsius, about 42 degrees Celsius, about 37 degrees Celsius, or other smaller, intermediate or larger thresholds are used.

Without being bound to theory, in accordance with an exemplary embodiment of the invention, a 6 mm long×1 mm wide transducer emitting ultrasound energy at an intensity of 100 Watts/square centimeter, generates about 11-24 Watts of excess heat (variation according to efficiency of operation) for removal. The amount of heat generated varies linearly with the size of the element and/or the intensity of emitted ultrasound energy.

In an exemplary embodiment of the invention, one or more sensors 308 are located, for example, downstream (e.g., according to the direction of flow 1220 of a liquid such a blood) relative to element 102. In an exemplary embodiment of the invention, sensor 308 measures the temperature of blood that has flowed 1220 over a surface 1224 of element 102. In an exemplary embodiment of the invention, the temperature of the blood that has flowed 1220 over surface 1224 is used as an estimate of the temperature of element 102.

In some embodiments, a liquid channel 1206 delivers a relatively cold liquid (e.g., saline, radio-opaque dye) to remove excess heat, for example, by causing the liquid to flow over surface 1224 of element 102. Optionally, the volume and/or frequency (e.g., pattern) of the liquid released (e.g., manually by a user, automatically by a controller) is estimated according to feedback of the temperature of element 102. Optionally, sensor 308 measures the temperature of the liquid after it has flowed over surface 1224.

In some embodiments, a heat conductor 1208 removes heat from element 102, inside catheter 1222. Optionally, heat conductor 1208 circulates a relatively cold fluid (e.g., saline, dye) towards element 102 to remove excess heat that is then transferred away from element 102 by the circulating fluid (e.g., direction arrows of system 1208).

Figure 15C:
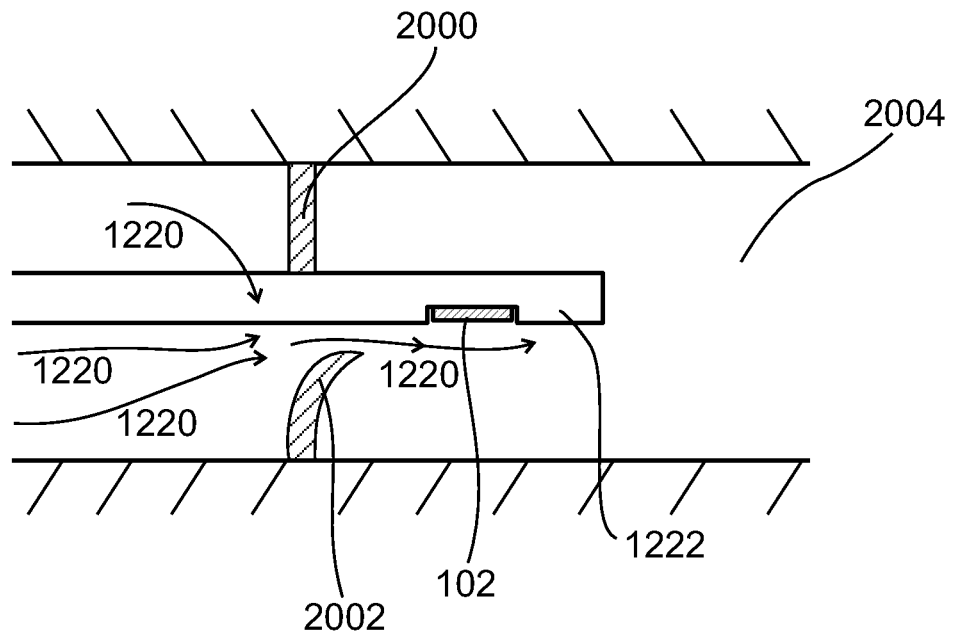
FIGS. 15A-C illustrate some embodiments of elements to cool and/or control the flow of a fluid over the transducer element, in accordance with an some embodiments of the invention.
Figure 15A:
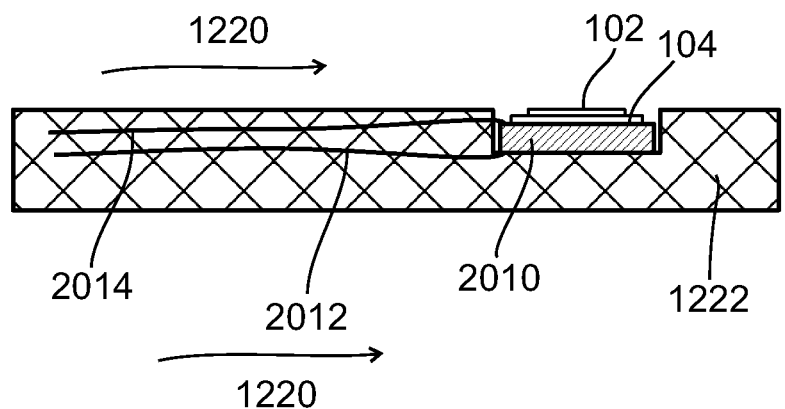

As illustrated in FIG. 15A, in some embodiments of the invention, a thermoelectric cooler 2010 (e.g., electrified by wires 2014) thermally coupled to element 102, is used to relatively increase the rate and/or amount of heat removed from element 102. Optionally, cooler 2010 acts as a housing.

In some embodiments of the invention, cooler 2010 is thermally coupled to a heat sink, for example, comprising one or more braids 2012 of catheter 1222 shaft. Optionally, braids 2012 are made out of a thermally conductive material, such as metal (e.g., silver, gold, nickel, steel, copper, platinum). Optionally, braids 2012 are thermally coupled to blood flowing 1220 on the surface of catheter 1222. A potential advantage of braids 2012 is the ability to spread heat from element 102 onto a relatively large surface area of catheter 1222, where it can be transferred to blood and/or other fluids (e.g., saline, urine, water, angiography contrast fluids, cerebrospinal fluid, lymph, mucous, stomach acid).

Figure 15B:
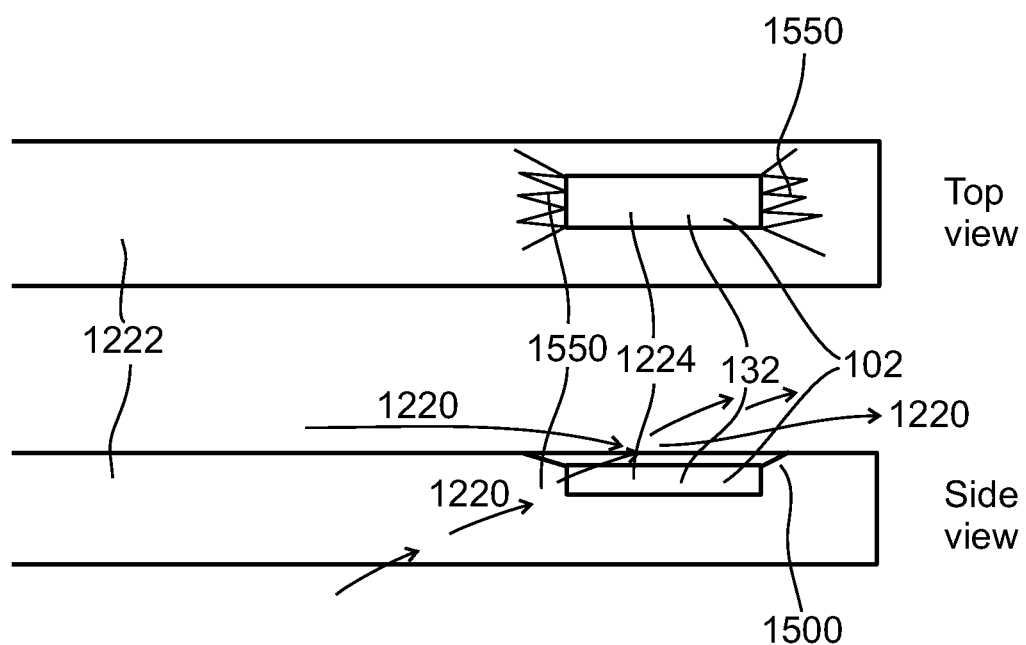

As illustrated in FIG. 15B, in some embodiments of the invention, one or more flow channels 1550 (e.g., grooves and/or indentations) formed at the surface of catheter 1222 direct flow of a fluid (e.g., blood) over the treatment surface 1224 and/or side 132 of element 102, for example, to transfer heat from element 102 to the fluid.

FIG. 15C illustrates a design for a flow controller 2000 to control (e.g., increase and/or decrease) flow 1220 of a fluid (e.g., blood) over element 102, for example, to cool element 102 by increasing the rate of heat transfer to the blood, in accordance with some embodiments of the invention. In some embodiments, flow controller 2000 is manually controlled by a user and/or automatically controller by a controller.

In some embodiments of the invention, flow controller 2000 comprises a gate (e.g., flap) 2002 to control blood flow 1220 over element 102, for example, by increasing and/or decreasing the cross sectional area of gate 2002 through which blood can flow 1220. Alternatively or additionally, controller 2000 controls blood flow 1220 by increasing and/or decreasing the cross sectional area of vessel 2004, for example, by inflating and/or deflating a balloon.

Another potential advantage of increasing and/or forming flow 1220 of a fluid (e.g., blood, saline) over element 102 is to reduce and/or prevent the formation of thrombus on element 102.

Kit

In some embodiments of the invention, catheters 1222 are sold as a kit, for example, there are multiple catheters 1222 to choose from for the treatment procedure. Optionally, the kit contains catheters 1222 having elements 102 designed for different treatment frequencies, for example, 10 Mhz, 20 Mhz, or other smaller, intermediate or larger frequencies. Optionally or additionally, catheters 1222 have different lengths for different anatomical treatment positions, for example, 55 cm to reach the renal artery, 95 cm to reach the carotid artery. Optionally or additionally, catheters 1222 are designed for specific anatomical treatment locations, for example, having elements 102 located at different positions on catheter 1222 such as to treat renal nerves at the renal artery ostium. Optionally or additionally, some catheters 1222 have elements 102 that can perform imaging functions.

Exemplary Control System

FIG. 16 illustrates an ultrasound treatment system 1600, in accordance with an exemplary embodiment of the invention. System 1600 provides for the control of the ultrasound treatment and/or monitoring of the treatment using catheter 1222.

In an exemplary embodiment of the invention, an operator (e.g., physician performing the procedure) programs a controller 1602 (e.g., computer) for treatment using a user interface 1604 (e.g., keyboard, mouse, monitor). Optionally, treatment is monitored, for example, by viewing feedback parameters on interface 1604.

In an exemplary embodiment of the invention, one or more functions and/or parameters and/or settings are programmed and/or set into controller 1602, for example:

Frequency of the ultrasound energy produced by vibration of element 102, for example, by a sinusoidal wave form.

Intensity is the produced ultrasound energy divided by the surface area of element 102.

Impedance of element 102.

Pulse duration is the length of a pulse measured in time.

Duty cycle is the percentage of time in a pulse that ultrasound energy is transmitted.

Duration of treatment is the time during which US energy is being delivered.

Acoustic feedback is feedback obtained by analyzing returning ultrasound signals, for example, the voltage across element 102 as a function of time.

Flow rate is the estimated (e.g., average) rate of flow of fluid (e.g., blood) across the surface of element 102 and/or the wall of the treatment target (e.g., blood vessel).

Efficiency is the estimated efficiency of converting electrical energy into ultrasound energy by element 102.

Temperature of operation is the approximate temperature of element 102 and/or the liquid (e.g., blood, saline) that should not be exceeded.

Cooling system cools element 102 to the temperature of operation. Optionally, cooling system is used in combination with blood flow.

Impulse excitation is the application of an impulse function (e.g., delta function) to element 102, causing element 102 to vibrate with a decreasing amplitude. In some embodiments of the invention, the integrity of system 300 is verified and/or checked by applying an impulse function (e.g. delta function) to element 102, resulting in a voltage pattern across element 102 (e.g. vibration and/or ringing pattern) over time. Optionally, the voltage pattern is used to estimate the reduction in efficiency of element 102, for example, by using a calibration look-up table, by performing calculations. The reduction in efficiency can be a result of, for example, one or more of, foreign material on surface of element 102 (e.g. thrombus), element 102 contacting the vessel wall, mechanical damage to element 102.

Navigation system controls the movement and/or positioning and/or orientation of catheter 1222 and/or transducer 300.

Treatment pattern is the combination of one or more of the above variables.

Pressure is the pressure of the liquid (e.g., blood) during treatment and/or imaging.

Electric power is the applied power to the transducer.

Reflected electric power from the transducer back to the controller.

Voltage is the measured and/or applied voltage on the transducer.

Current is the measured and/or applied current in the transducer.

| Parameter | Theoretical range | Exemplary Treatment range | Exemplary Treatment sub range |
|---|---|---|---|
| Frequency (MHz): | | | |
| Treatment | 1-60 | 8-30 | 10-22 |
| Imaging | 1-60 | 10-60 | 10-25 |
| Intensity (Watts/sq cm) | 1-200 | 10-100 | 10-60 |
| Duty cycle (%) | 0.1-100 | 10-100 | 50-100 |
| Pulse duration (seconds) | 0.01-1000 | 0.1-4 | 0.1-2 |
| Duration of treatment (Seconds) per location | 0.1-1000 | 2-120 | 3-60 |
| Efficiency (%) | 1-70% | 20-70% | 35-70% |
| Temperature (Celsius) | 10-100 | 15-80 | 25-80 |

In an exemplary embodiment of the invention, controller 1602 produces an electrification waveform that is sinusoidal according to the set "Frequency" with an amplitude associated with the set "Intensity".

In an exemplary embodiment of the invention, controller 1602 monitors and/or maintains one or more set parameters, according to one or more adjustable parameters. Optionally, controller 1602 adjusts one or more parameters, for example, according to changes (e.g., increase and/or decrease of 10%) between the current measurement and/or one or more previous measurements. Controller 1602 automatically selects one or more parameters to adjust, for example, according to one or more of, a look-up table (e.g., stored in a memory), calculations, using feedback (e.g., slowly changing a parameter and/or monitoring expected changes).

In an exemplary embodiment of the invention, power unit 1606 provides voltage and/or current (e.g., alternating and/or oscillating) to electrodes 302 and/or 304, causing element 102 to vibrate (e.g., expand and/or contract) at the set frequency, outputting a set power intensity.

Potential Advantages of Some Embodiments

Further details of the system described herein can be found in the related applications. For example, "TISSUE TREATMENT" (PCT Patent Application No. PCT/IB2011/054640 filed on Oct. 18, 2011) describes a method and an apparatus for tissue treatment. For example, "AN ULTRASOUND TRANSCEIVER AND USES THEREOF" (PCT Patent Application No. PCT/IB2011/054636 filed on Oct. 18, 2011) describes a method for feedback and control. For example, "AN ULTRASOUND TRANSCEIVER AND COOLING THEREOF" (PCT Patent Application No. PCT/IB2011/054641 filed on Oct. 18, 2011 describes cooling of the ultrasonic element. For example, "SEPARATION DEVICE FOR ULTRASOUND ELEMENT" (PCT Patent Application No. PCT/IB2011/054638 filed on Oct. 18, 2011) describes preventing contract between the ultrasonic element and the blood vessel wall. For example, "ULTRASOUND TRANSCEIVER AND USES IN DETECTION" (PCT Patent Application No. PCT/IB2011/054639 filed on Oct. 18, 2011) describes ultrasonic imaging.

Some embodiments have one or more of the following exemplary advantages:

Relatively faster treatment, for example, a treatment duration of 5-30 seconds per treatment region, or other smaller, larger or intermediate ranges can be used.

Relatively small number of treatment regions per artery for renal denervation, for example, 4 treatment regions, or other smaller, intermediate or larger number of treatment regions are used.

Remote and/or localized effect, for example,

Accurate control of the thermal effect and/or location, such as good control on the location and/or size of the artery tissue damage by therapeutic parameters.

Ability to treat relatively large continuous areas in the arterial wall.

A treatment option for short artery stumps and/or for short total treatment durations (e.g., 5-10 minutes vs 20 minutes for RF treatments).

The thermal effect volume in the tissue is relatively far from the transducer face (e.g., media, adventitia, vasa-vasorum, peri-adventitia, adventitia nerves, peri-adventitia nerves, peri-adventitia capillaries).

Targeting tissues in varying distances from the transducer face according to treatment parameters. For example, applying the thermal effect in tissues located about 5 mm or more from the lumen wall (e.g., intima layer). A relatively far effect is relevant for example, for achieving peripheral nerves blocks from inside the peripheral arteries.

Non-targeted tissues on the beam path to the target tissue are not damaged and/or are selectively damaged (e.g. according to a margin of safety), for example, the endothelium, basal membrane and/or internal elastic lamina.

Possibility for varying levels of thermal modulation of the target tissue. For example, partial damage to nerves and/or other target tissues, in a controlled manner and different effect levels. Potentially, partial nerve injury can be controlled, that might lead to nerve recovery, either partially or entirely.

Tissue selectivity, for example, highly selective remote thermal effect in nerve bundles, such as nerves that are covered with thick fat tissue. For example as used in a Renal Denervation procedure in the Renal Artery ostium.

Treatment features suitable for Renal Denervation include:

The ability to work very close to the renal artery ostium, for example, <10 [mm], or other smaller, intermediate or larger values.

The ability to work in short arteries, for example, <20 [mm], or other smaller, intermediate or larger values, The ability to work in small arteries, for example, 4-3 [mm], or other smaller, intermediate or larger values, Safety issues Relatively safer treatment.

The temperature of the blood that flows over the ultrasonic transducer can be controlled to not exceed a temperature threshold of 50 degrees Celsius (or other smaller, intermediate or larger numbers) while working in the maximal allowed operation intensity level, for example, 50 [W/cm^2], or other smaller, intermediate or larger intensity levels.

The temperature of the blood that flows over the ultrasonic transducer can be controlled to not exceed a temperature threshold of over 43 degrees Celsius (or other smaller, intermediate or larger numbers), for example, while working in the therapeutic operation intensity level 30 [W/cm^2], or other smaller, intermediate or larger intensity levels. In some embodiments, there is no need to add external cooling such as by saline injection.

The therapeutic treatment on the blood vessel wall is done with no mechanical contact with the vessel wall, thereby reducing or eliminating the danger of damaging the vessel wall or disrupting any pathologies on the wall (e.g., atherosclerotic plaques). For example, reducing the risk of arterial perforation and/or mechanical damage that might cause a narrowing in the vessel, plaque tear and/or emboli.

Localized and/or controlled effects specifically in the targeted treatment volume, preventing and/or reducing non-controlled energy effects in other tissues.

Blocking of the blood flow during the treatment is optional, and in some embodiments, is not required.

Treatment of a single artery location (e.g., longitudinally) in one or more circumferential directions, potentially, significantly reducing and/or preventing stenosis.

Preventing and/or reducing damage to the artery due to repeating treatment 2-3 times (or more) at the same region/direction, such as due to a mistake.

Prevent and/or reduce interference with implanted electronic medical devices (e.g., pacemakers, defibrillators).

Clinical implications, for example, relatively lower pain during treatment as a result of relatively faster blocking of nerves, with no electric excitation of the target nerve and/or no effect on other nerves. Potentially reducing sedation and/or anesthesia.

Relatively shallow learning curve, as leverages existing operator skill sets.

Many applications and/or ability to treat a wide range of clinical disorders.

Treatment option for a wide range of patients, such as high risk populations, for example as those suffering from vascular pathologies. Ability to treat in arteries with plaques and/or stents.

Ability to obtain a partial clinical effect (vs. complete effect). Potentially suitable for patients with milder disease, such as mild hypertension.

Feedback availability during treatment, such as information on the direction and location of the applied energy, catheter and the therapeutic catheter tip:

Easy control capability and a clear direction and location of the ultrasonic ray and/or catheter location to carry out treatment, such as according to the ultrasonic echo reflection analysis.

Ability to control the circumferential direction of the artery tissue damage.

Continues information (e.g., ultrasonic measurement) on the position of the catheter tip, such as from the artery wall during treatment.

Automatic detection of unwanted and/or risky movement of the catheter during treatment.

General

It is expected that during the life of a patent maturing from this application many relevant ultrasound transducers will be developed and the scope of the term transducer is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An ultrasound catheter for intrabody medical therapy comprising:
    an element adapted to emit ultrasound energy;
    at least two electrodes configured to apply a voltage across at least some volume of said element; and
    a support board, wherein said element is coupled to said support board at 0.06%-0.72% of a surface area of said element; and wherein said coupling between said element and said support board suspends said element at a distance of at least 0.1 micrometer above said board.

2. A catheter according to claim 1, wherein a gas bubble is retained in a gas bubble containment area defined in a space between said board and said element, said space being open to the outside of the catheter.

3. A catheter according to claim 2, wherein at least some surface area of at least said element and said board comprise a coating adapted to retain said bubble to said element.

4. A catheter according to claim 3, wherein said coating comprises parylene.

5. A catheter according to claim 2, wherein said board comprises a depression or an aperture, and said element is positioned over at least some volume of said depression or said aperture.

6. A catheter according to claim 1, wherein said element is rectangular.

7. A catheter according to claim 2, wherein said element comprises irregularities on a surface to couple said bubble to said element by increasing an area of said surface.

8. A catheter according to claim 2, wherein said gas comprises selecting from the group consisting of: air, oxygen, nitrogen, carbon dioxide, carbon tetrafluoride.

9. A catheter according to claim 2, further comprising at least two bubbles coupled to a side of said element.

10. A catheter according to claim 2, further comprising a housing, said housing coupled to said board.

11. A catheter according to claim 10, wherein said housing comprises a heat sink thermally coupled to said element.

12. A catheter according to claim 1, further comprising:
    a canopy surrounding said element; and
    fluid between said element and said canopy.

13. A catheter according to claim 12, wherein said fluid comprises a circulating fluid.

14. A catheter according to claim 1, wherein said ultrasound emission element is further adapted to receive ultrasound energy.

15. A catheter according to claim 1, wherein said element is configured to produce a non-diverging ultrasound beam.

16. A catheter according to claim 1, wherein said element is suspended by a material raised above a surface of said board.

17. A catheter according to claim 16, wherein said material includes copper.

18. A catheter according to claim 16, wherein said material includes an electrically conductive glue.

19. A catheter according to claim 1, wherein element is suspended over an aperture or a depression in said board by walls of said aperture or depression.

20. A catheter according to claim 1, wherein said element is suspended over said board along the periphery of said element.

21. A catheter according to claim 1, wherein said element is suspended over said board away from the periphery of said element.

22. A catheter according to claim 1, wherein said board further comprises at least one heat conductive element thermally coupled to said element.

23. A catheter according to claim 1, comprising two or more elements adapted to transmit ultrasound energy, at least one of said two or more elements is supported above said board, and at least one gas bubble coupled to at least one of said two or more elements.

24. A catheter according to claim 23, wherein a cross section of said support board is annular.

25. A catheter according to claim 1, further comprising:
    two or more elements adapted to emit ultrasound energy, at least two of said two or more elements are supported by said board;
    at least two electrodes configured to apply a voltage across at least some volume of said two or more elements; and
    a gas bubble coupled to at least two elements of said at least two elements.

26. A catheter according to claim 25, wherein said two or more elements are used as a phased array.

27. An ultrasound catheter according to claim 1, wherein said board comprises at least one channel to direct flow of a fluid between said board and said element.

28. An ultrasound catheter according to claim 1, wherein said coupling between said element and said support board is at a face of said element opposite an emitting face of said element.

* * * * *